(12) United States Patent
Sinosich

(10) Patent No.: US 6,172,198 B1
(45) Date of Patent: *Jan. 9, 2001

(54) PAPP-A, ITS IMMUNODETECTION AND USES

(75) Inventor: Michael Joseph Sinosich, 9 Sirius Place, Engadine, Sydney, NSW 2233 (AU)

(73) Assignees: Northern Sydney Area Health Service; Michael Joseph Sinosich, both of (AU)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/957,317

(22) PCT Filed: Mar. 21, 1994

(86) PCT No.: PCT/AU94/00139

§ 371 Date: Nov. 13, 1995

§ 102(e) Date: Nov. 13, 1995

(87) PCT Pub. No.: WO94/21686

PCT Pub. Date: Sep. 29, 1994

Related U.S. Application Data

(63) Continuation of application No. 08/530,210, filed on Nov. 13, 1995, now abandoned.

(30) Foreign Application Priority Data

Mar. 19, 1993 (AU) .................................................. PL 7926

(51) Int. Cl.[7] .................................................. C07K 16/00
(52) U.S. Cl. ............................ 530/387.9; 530/388.25; 530/389.3; 435/7.91; 435/7.92; 435/7.95; 435/806; 435/810
(58) Field of Search ........................... 530/387.9, 388.25, 530/389.3; 424/145.1, 130.1; 435/7.1, 7.91, 7.92, 7.94, 7.95, 806, 810, 975; 436/510, 513, 518, 804, 523–531, 65, 814, 906

(56) References Cited

U.S. PATENT DOCUMENTS 4,558,035  12/1985  Johnson ................................. 514/8

FOREIGN PATENT DOCUMENTS

| 25177/88 | 6/1989 | (AU) . |
|---|---|---|
| 156266 | 10/1985 | (EP) . |
| 283606 | 9/1988 | (EP) . |
| 316919 | 5/1989 | (EP) . |
| 59-175-438 | 10/1984 | (JP) . |
| 1675773 | 9/1991 | (SU) . |
| WO 86/00623 | 1/1986 | (WO) . |
| WO 90/07937 | 7/1990 | (WO) . |

OTHER PUBLICATIONS

M. Sinosich et al, "Pregnancy–Associated Plasma Protein A Interaction with Heparin: A Critical Appraisal", *Gynecol. Obstet. Invest.*, 32(2):72–77 (Oct., 1991) [Sinosich I].

M. Sinosich et al, "A Baboon Model for Pregnancy–Associated Antigens (PAAP–A, PP5, PP14)", *Arch. Gynecol. Obstet.*, 247(2):53–62 (1990) [Sinosich II].

M. Sinosich et al, "Characterization of Pregnancy–Associated Plasma Protein–A: Comparison with a2–Macroglobulin", *Biochem. Int'l.*, 20(3):579–589 (1990) [Sinosich III].

M. Sinosich, "Molecular Characterization of Pregnancy–Associated Plasma Protein–A by Electrophoresis", *Electrophoresis*, 11(1):70–78 (1990) [Sinosich IV].

M. Sinosich et al, "RU486 Induced Suppression of Placental Neutrophil Elastase Inhibitor Levels", *Placenta*, 10(6):569–578 (1989) [Sinosich V].

M. Sinosich et al, "Radioimmunoassay for Pregnancy–Associated Plasma Protein A", *Clin. Chem.*, 28(1):50–53 (1982) [Sinosich VI].

M. Sinosich et al, "Comparative Studies of Pregnancy Associated Plasma Protein–A and a2–Macroglobulin Using Metal Chelate Chromatography", *Biochem. Int'l.*, 7(1):33–42 (Jun., 1983) [Sinosich VII].

M. Sinosich et al, "Pregnancy–Associated Plasma Protein A in Human Ovarian Follicular Fluid", *J. Clin. Endocrinol. and Metabolism*, 58(3):500–504 (Mar., 1984) [Sinosich VIII].

M. Sinosich et al, "Pregnancy–Associated Plasma Protein–A in Human Seminal Plasma", *Prot. Biol., Fluids*, 32:289–292 (1985) [Sinosich VIX].

M. Sinosich et al, "Specific Inhibition of Human Granulocyte Elastase by Human Pregnancy Associated Plasma Protein–A", *Biochem. Int'l.*, 5(6):777–786 (Dec., 1982) [Sinosich X].

M. Sinosich et al, "Potential Role of Pregnancy–Associated Plasma Protein–A in Human Reproduction", *J. Reprod. Immunol.*, 10:55–65 (1987) [Sinosich XI].

M. Sinosich et al, "Pregnancy Associated Plasma Protein A: A Barrier to Maternal Proteolytic Attack", in *In Vitro Fertilization, Embryo Transfer and Early Pregnancy*, ed. R. F. Harrison et al, MTP Press Ltd., pp. 209–212 (1984) [Sinosich XII].

(List continued on next page.)

Primary Examiner—Sheela Huff
(74) Attorney, Agent, or Firm—Howson and Howson

(57) ABSTRACT

This invention concerns PAPP-A, its immunodetection and the clinical benefits of such immunodetection. Specifically, the invention includes monoclonal antibodies against PAPP-A and the use of these antibodies to detect PAPP-A at a very early stage of pregnancy. The invention also covers the use of the monoclonal antibodies for the detection of specific types of cancer and Down's Syndrome pregnancies.

35 Claims, 12 Drawing Sheets

OTHER PUBLICATIONS

M. Sinosich, "Past, Present and Future of Pregnancy—Associated Plasma Protein–A (PAAP–A)", *Placental and Endometrial Proteins*, pp. 11–18 (1988) [Sinosich XIII].

M. Sinosich et al, "The Prediction of Pregnancy Failure by Measurements of Pregnancy–Associated Plasma Protein A (PAAP–A) Following in Vitro Fertilization and Embryo Transfer", *Fertil. Steril.*, 40(4):539–541 (Oct., 1983) [Sinosich XIV].

M. Sinosich et al, "Monitoring of Postimplantation Embryo Viability Following Successful in Vitro Fertilization and Embryo Transfer by Measurement of Placental Proteins", *Fertil. Steril.*, 44(1):70–74 (Jul., 1985) [Sinosich XV].

M. Sinosich et al, "Circulating and Tissue Concentrations of Pregnancy–Associated Plasma Protein–A (PAPP–A) in Tubal Ectopic Gestation", *J. Clin. Reprod. and Fertil.*, 3:311–317 (1985) [Sinosich XVI].

M. Sinosich et al, "Pregnancy Associated Plasma Protein–A: Interaction with Heparin in Crossed Affinity Immunoelectrophoresis", *Aust. N. Z. J. Med.*, 11(4):429–433 (Aug., 1981) [Sinosich XVII].

M. Sinosich, "Biological Role of Pregnancy–Associated Plasma Protein–A in Human Reproduction", in *Proteins of the Placenta*, 5th Int. Congr. on Placental Proteins, Annecy, ed. P. Bischof et al, (Karger, Basel), pp. 158–183 (1985) [Sinosich XVIII].

T–M. Lin et al, "Measurement of Pregnancy–Associated Plasma Proteins during Human Gestation", *J. Clin. Invest.*, 54(3):576–582 (Sep., 1974) [Lin I].

T–M. Lin et al, "Characterization of Four Human Pregnancy–Associated Plasma Proteins", *Am. J. Obstet. Gynecol.*, 118(2):223–236 (Jan., 1974) [Lin II].

T–M. Lin et al, "Three Pregnancy–Associated Human Plasma Proteins: Purification, Monospecific Antisera and Immunological Identification", *Int. Arch. Allergy*, 47:35–53 (1974) [Lin III].

T–M. Lin et al, "Characterization and Purification of Human Pregnancy–Associated Plasma Proteins", *Fed. Proc.*, 32:2307 (Biochemistry, Abstract No. 2307) (1973) [Lin IV].

P. Bischof et al, "Immunological Heterogeneity of Pregnancy–Associated Plasma Protein–A (PAPP–A). Effects on the Radioimmunoassay of PAPP–A", *British Journal of Obstetrics and Gynaecology*, 96(7):870–875 (Jul., 1989) [Bischof I].

P. Bischof et al, "Pulsatile Secretion of Pregnancy–Associated Plasma Protein–A (PAPP–A) in Non–Pregnant Women", *British Journal of Obstetrics and Gynaecology*, 93:600–605 (Jun., 1986) [Bischof II].

P. Bischof et al, "Circulating Levels of Pregnancy–Associated Plasma Protein–A (PAPP–A) and Human Chorionic Gonadotrophin (hCG) in Intrauterine and Extrauterine Pregnanceis", *British Journal of Obstetrics and Gynaecology*, 90:323–325 (Apr., 1983) [Bischof III].

P. Bischof, "Purification and Characterization of Pregnancy Associated Plasma Protein A (PAPP–A)", *Arch. Gynecol.*, 227:315–332 (1979) [Bischof IV].

J. Westergaard et al, "Pregnancy–Associated Plasma Protein A: A Possible Marker in the Classification and Prenatal Diagnosis of Cornelia De Lange Syndrome", *Prenatal Diagnosis*, 3:225–232 (1983) [Westergaard I].

J. Westergaard et al, "Pregnancy–Associated Plasma Protein–A in the Prediction of Early Pregnancy Failure", *Am. J. Obstet. Gynecol.*, 145:67–70 (1983) [Westergaard II].

M. Davey et al, "Interaction Between Heparin and Human Pregnancy–Associated Plasma Protein A (PAAP–A); A Simple Purification Procedure", *Analy. Biochem.*, 131(1):18–24 (1983).

A–M. Schindler et al, "Histochemical Localization of Pregnancy–Associated Plasma Protein A in Fetal, Infant, and Adult Organs and Comparison Between Antisera", *Gynecol. Obstet. Invest.*, 18:88–94 (1984).

B. Brambati et al, "Ulatrasound and Biochemical Assessment of First Trimester Pregnancy", in *The Embryo: Normal and Abnormal Development and Growth*, ed. M. Chapman et al, Springer–Verlag, pp. 181–194 (1990).

R. Sutcliffe et al, "The Use of Antibody Affinity Chromatography and Other Methods in the Study of Pregnancy–Associated Proteins", in *Placental Proteins*, ed. A. Klopper et al, Springer–Verag Berlin/New York, pp. 55–70 (1979).

J. Folkersen et al, "Purification of Pregnancy–Associated Plasma Protein–A by a Two Step Affinity Chromatographic Procedure", *Placenta*, 2:11–18 (1981).

F. Tsakok et al, "Prognostic Significance of the New Placental Proteins in Trophoblastic Disease", *British Journal of Obstetrics and Gynaecology*, 90:483–486 (May, 1983).

N. Wald et al, "First Trimester Concentrations of Pregnancy Associated Plasma Protein A and Placental Protein 14 in Down's Syndrome", *BMJ*, 305:28 (Jul., 1992).

T. Kristensen et al, "Amino Acid Sequence of Human Pregnancy–Associated Plasma Protein–A Derived from Cloned cDNA", *Biochemistry*, 33(6):1592–1598 (1994).

N. Chegini et al, "The Presence of Pregnancy–Associated Plasma Protein–A in Human Corporea Lutea: Cellular and Subcellular Distribution and Dependence on Reproductive State", *Biology of Reproduction*, 44(1):201–206 (1991).

L. Pinto Furtado et al, "The Development and Validation of a Radioimmunoassay for Human Pregnancy–Associated Plasma Protein A (PAPP–A)", *Arch. Gynecol.*, 236(2):83–91 (1984).

E. Mowles et al, "A Two–Site Immunoradiometric Assay for Human Pregnancy–Associated Plasma Protein A (PAAP–A) Using Monoclonal Antibodies", *J. Immunol. Meth.*, 95(1):129–133 (1986).

Harris et al, TIBTECH vol. 11 p. 42 Feb. 1993.*

Waldmann, Science vol. 252 p. 1657 Jun. 1991.*

* cited by examiner

FIGURE 1

N-terminal amino acid sequnce of human PAPP-A.

Glu-Ala-Arg-Gly-Ala-Pro-Glu-Glu-Pro-Ser-Pro-Pro-Ser

Figure 3 Sandwich PAPP-A assay formats

```
                           SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 13 amino acids
        (B) TYPE: amino acid
        (C) STRANDEDNESS:
        (D) TOPOLOGY: Not Relevant
```

-continued (ii) MOLECULE TYPE: peptide (xi) SEQUENCE DESCRIPTION: SEQ ID NO:1:

Glu Ala Arg Gly Ala Pro Glu Glu Pro Ser Pro Pro Ser
1               5                   10

PAPP-A, ITS IMMUNODETECTION AND USES

This is a continuation of U.S. patent application Ser. No. 08/530,210, filed Nov. 13, 1995 now abandoned, which is a 371 of PCT/AU94/00139, filed Mar. 21, 1994, which claims priority of Australian Application No. PL 7926 filed on Mar. 19, 1993.

Technical Field

The present invention relates to: purified pregnancy-associated plasma protein-A (PAPP-A); PAPP-A variants; polynucleotides encoding PAPP-A; isolation and purification of PAPP-A; monoclonal antibodies raised against PAPP-A; use of these monoclonal antibodies and PAPP-A for diagnostic purposes, including a kit for the assaying of PAPP-A levels in a sample; use of PAPP-A measurement, in conjunction with another marker of trophoblastic activity (such as chorionic gonadotrophin or its subunits), to discriminate between feto-placental abnormalities, such as Trisomy 21 (Down Syndrome), and oncological status, such as Gestational Trophoblastic Diseases (GTD); use of PAPP-A monoclonal antibodies to isolate fetal trophoblast cells for prenatal fetal cytogenetic diagnosis; use of PAPP-A, as a target antigen for active immunological contraception, and PAPP-A antibodies as a passive contraceptive vaccine; use of PAPP-A as a medicament and a medicament comprising an effective amount of PAPP-A.

BACKGROUND ART

Placental proteins are those proteins expressed during pregnancy by the human placenta. The ability to detect the presence and concentrations of these proteins has the potential to provide a reliable diagnostic marker of fertilisation, implantation and pregnancy prognosis.

A number of placental proteins have now been isolated and at least partially characterised. These include—human chorionic gonadotropin (hCG), pregnancy-specific $\beta_1$—glycoprotein (SP1), placental protein 5 (PP5), early pregnancy factor (EPF), and pregnancy-associated plasma protein-A (PAPP-A)[1.]

These proteins are detectable, in maternal blood, at various stages during pregnancy. For example, EPF activity is detectable within 24 hours after conception. HCG is measurable just after implantation, at about 9 to 11 days post-ovulation, SP1 is detectable from 18 to 23 days post-ovulation. In singleton pregnancies, PAPP-A can be detected approximately 28–32 days post-ovulation[2].

Placental proteins are also detectable for varying periods during pregnancy. For example, EPF is detectable at least for the first half of pregnancy, whereafter activity declines until it is totally absent during the third trimester in some women. HCG levels rise rapidly to peak at about 8 to 12 weeks gestation. The levels of SP1 rise exponentially with peak concentrations being reached at term pregnancy. Like SP1, PAPP-A concentrations also rise exponentially in the first trimester of pregnancy to peak at term[2].

Whilst it has been suggested to measure the presence of placental proteins for early detection of pregnancy (for example, see European Application 316919), there is a growing body of documented evidence that at least some placental proteins, particularly PAPP-A, may be used to predict pregnancy viability, including early pregnancy failure, extra-uterine gestations, aneuploid and/or abnormal pregnancies, such as Down's Syndrome[3] and Cornelia de Lange Syndrome[4].

PAPP-A, first described almost two decades ago[1], is a large zinc containing glycoprotein, rich in carbohydrate, with many physicochemical similarities to a 2-macroglobulin[5]. It has been detected in maternal circulation[5], pre-ovulatory ovarian follicular fluid[6], in seminal plasma[7] and blood of patients with trophoblastic disease[8].

PAPP-A is a homotetramer, with each monomeric subunit having a molecular weight of approximately 200 kDa. The subunits are linked by disulphide bonds to form dimers of approximately 400 kDa. Native PAPP-A consists of two dimers linked by Van der Waals (ionic) forces. Native PAPP-A has a molecular weight of approximately 820 kDa, regardless of whether it is derived from follicular fluid, seminal plasma, oncological or normal placental tissue[7]. The mature protein has a 2-$\beta$1 electrophoretic mobility, with an isoelectric point of approximately 4.2–4.5[9]. It is a noncompetitive and potent inhibitor of human granulocyte elastase[10].

It has been suggested that the biological function of PAPP-A is to act as a local protective barrier against host (maternal) phagocytic-proteolytic defences to either inseminated sperm or the developing feto-placental unit[11]. This may be due to PAPP-A forming a protective sheet around the chorionic villus at the utero-placental interface[12]. Disruption of this protective layer may explain the correlation between depressed PAPP-A levels and pregnancy failure. PAPP-A may also play a role in zinc homeostasis[5].

Schindler and Bischof[13] suggested that the protein was ubiquitous and, therefore, of little practical use in pregnancy viability diagnosis.[14,15] However, it was subsequently shown that these results were due to impure PAPP-A isolates, due to the difficulties in isolating PAPP-A free of a 2-macroglobulin, and polyspecific antisera[16].

Sinosich et al.[3] first suggested that a depressed or undetectable PAPP-A level in maternal blood was diagnostic of pregnancy failure. Later, Sinosich et al.[17] showed that, of five successful in vitro fertilisation volunteers, three patients with normal pregnancy outcome had circulating PAPP-A levels within the 80% confidence limits of the normal range. By contrast, circulating PAPP-A levels in the patient who spontaneously aborted at seventeen weeks were below the tenth percentile throughout the entire gestation. In the fifth patient, who had a ruptured ectopic pregnancy, PAPP-A could not be detected at any stage during the pregnancy. These findings were complimented by Westergaard et al. (1983)[18], who reported that, in a sample group of 51 patients, who conceived spontaneously, with vaginal bleeding in the first half of pregnancy, concentrations of PAPP-A were consistently lower in pregnancies which failed. Similarly, Sinosich et al. (1985)[19] showed that, in a group of 21 women who conceived by in vitro fertilisation, PAPP-A levels were consistently depressed, for many weeks, in those women whose pregnancies failed. The same group showed that, of forty seven serum samples obtained from patients with a tubal pregnancy, only two were positive for PAPP-A, indicating that severely depressed or undetectable serum PAPP-A levels were an aid in the diagnosis of extra-uterine pregnancy.[20]

In 1990, Brambati et al.[21] reported that first trimester maternal serum concentrations of PAPP-A were low in pregnancies associated with Down's syndrome. Later, Wald et al. (1992)[3] confirmed that PAPP-A concentration was significantly lower in women with Down's syndrome pregnancies compared to PAPP-A levels in a control group of normal pregnancies.

It has also been reported that PAPP-A was detected in the circulation of patients with hydatiform mole[2], suggesting a potential role for PAPP-A quantification in diagnosis and management of certain tumours.

These findings demonstrate the potential diagnostic value of measuring PAPP-A levels for monitoring feto-placental status. Moreover, in view of the increasing use of in vitro fertilisation techniques, and the relatively high proportion of early pregnancy failures associated with these techniques, the measurement of PAPP-A levels to monitor pregnancy viability and thereby minimise patient trauma is clinically advantageous.

Lin. et al. (1974)[22] described the use of an electroimmunoassay to measure PAPP-A levels in advanced pregnancy. This assay was insensitive and limited to latter stages of pregnancy. Sinosich et al. (1982)[2] and (1984)[6] described the first sensitive radioimmunoassay (RIA) which detected PAPP-A in serum obtained from first trimester pregnancies. This assay used radioactively labelled purified PAPP-A together with rabbit anti-human PAPP-A antiserum. The sensitivity of this RIA (2.9 µg/L) enabled PAPP-A detection in maternal blood after the first six weeks of pregnancy. The assay made it possible to detect PAPP-A in other fluids (amniotic fluid, seminal plasma, follicular fluid, gestational trophoblastic disease, culture media), previously beyond the limits of detection. This assay also made it possible to study the kinetics and physiology of maternal PAPP-A levels in the first trimester of pregnancy, a crucial stage for feto-placental development.

The PAPP-A RIA differed from standard protocols in that molecular size of tracer ($^{125}$I-PAPP-A; Mr 820 kDa) and immune complexes required modification of the separation phase. Optimal separation of antibody-bound from antibody-free tracer was achieved with second antibody— 7.5%(w/v) polyethylene glycol (PEG) solution, in the ratio of 2:1, 2nd antibody-PEG to assay reaction volume. Under these conditions, assay blank values could be reduced to 5–7%, whilst maximum binding would approach 60–70%.

The development of sensitive and reliable techniques for measuring PAPP-A is dependent on being able to isolate the protein in a sufficiently pure form and/or the generation of monospecific antibodies.

A number of methods for isolating and purifying PAPP-A have been described previously. For example, Lin. et al. (1974)[23] describe a procedure based on classical protein fractionation technology. This procedure utilised:

i) solubility;
ii) charge; and
iii) size.

This procedure was technically cumbersome and resulted in a low yield of impure material.

Bischof (1979)[24] described a method of isolating and purifying PAPP-A. This procedure utilised:

i) solubility;
ii) charge;
iii) lectin affinity;
iv) size fractionation; and
v) negative immunoaffinity.

This was even more cumbersome than the earlier procedure. The final product was still impure and yields remained low.

Sutcliffe et al.(1979)[25] and Folkersen et al. (1981)[26] described a purification method which used;

i) solubility;
ii) positive immunoaffinity chromatography (immobilised anti-PAPP-A antibodies); and
iii) size or charge, respectively.

Step (ii) is detrimental to PAPP-A integrity and neither procedure resulted in pure PAPP-A. Although the final yield was improved by this method, the quality of the protein yield was sacrificed.

Based on an interaction with heparin (Sinosich et al. 1981)[27], Sinosich et al. (1982)[10] reported the first application of heparin-Sepharose for PAPP-A purification. For the first time it was possible to prepare a high yield (22%) of highly purified PAPP-A. However, by more current and stringent criteria, this preparation was also found to be impure.

DISCLOSURE OF THE INVENTION

The inventor has developed a purification procedure which enables PAPP-A to be purified to a much higher degree than achieved with prior art purification techniques and in particular to a level which permits the amino-acid sequencing of the protein. The inventor has sequenced the first thirteen (13) N-terminal amino acids of human PAPP-A and this sequence is:

Glu-Ala-Arg-Gly-Ala-Pro-Glu-Glu-Pro-Ser-Pro-Pro-Ser [SEQ ID NO:9]

According to a first aspect of the present invention there is provided the protein PAPP-A, substantially free of other (primate) proteins, said PAPP-A being a homotetramer having a molecular weight of approximately 820 kiloDaltons and an isoelectric point of approximately 4.5, each monomeric subunit of the homotetramer having a molecular weight of approximately 200 kiloDaltons and an N-terminal amino-acid sequence of Glu-Ala-Arg-Gly-Ala-Pro-Glu-Glu-Pro-Ser-Pro-Pro-Ser [SEQ ID NO:1].

The ability to sequence the protein indicates that the preparation is at least 90% pure.

Biologically active proteins are usually only present in trace amounts in biological systems. Consequently, purification from naturally occurring sources is expensive and time consuming. Having purified PAPP-A to sufficient purity to obtain amino acid sequence for the protein, it is now possible for the first time to produce degenerate nucleotide probes which correspond to the determined amino acid sequence. These probes can then be used to detect nucleic acid encoding PAPP-A and clone it. At this level of purity PAPP-A can also be used as an antigen to raise antibodies to detect PAPP-A expressing clones.

Production of the PAPP-A protein by recombinant techniques and isolation of the DNA encoding PAPP-A also makes it possible to obtain a complete amino acid sequence for PAPP-A. The complete amino acid sequence can be used to determine appropriate sites for mutagenesis in the production of clinically useful PAPP-A variants.

According to a second aspect of the present invention there is provided a PAPP-A variant. Variants of PAPP-A in accordance with this invention are polypeptides which correspond to or comprise a portion of PAPP-A or have homology with the PAPP-A amino acid sequence.

For the purposes of this description "homology" between two peptide sequences connotes a likeness short of identity, indicative of a derivation of the first sequence from the second. In particular, a polypeptide is "homologous" to PAPP-A of the invention if a comparison of amino-acid sequences between the polypeptide and PAPP-A reveals an identity of greater than about 70%. Such a sequence comparison can be performed via known algorithms, which are readily implemented by computer.

According to a third aspect of the invention there is provided a polynucleotide encoding PAPP-A or a PAPP-A variant of the present invention.

According to a fourth aspect of the invention, there is provided a method for isolating and purifying PAPP-A, said method comprising:
 (i) applying the sample to a positive affinity chromatography on heparin-Sepharose;
 (ii) size fractionating the fractions obtained from step (i) on a gel filtration column; and
 (iii) applying the fractions obtained from step (ii) to an anion exchange column; and
 (iv) applying the fractions obtained from step (iii) to a matrix with immobilized antibodies.

According to a fifth aspect of the invention, there are provided monoclonal antibodies which recognise PAPP-A. Typically the monoclonal antibodies of this aspect recognise PAPP-A but do not significantly cross-react with immobilized heparin-Sepharose binding proteins extracted from normal male serum. Preferably the monoclonal antibodies are specific for PAPP-A. In particular, the inventor has developed five (5) monoclonal antibodies which specifically recognise five (5)distinct epitopes of the PAPP-A protein.

The first monoclonal antibody—clone 25-1—has been isotyped as $IgG_2$ (K light chain) with an affinity constant of $1.26 \times 10^{-9}$. Clone 25-1 reacts specifically with human PAPP-A but not with chimpanzee or rhesus PAPP-A.

The second monoclonal antibody—Clone 27-66, isotyped as IgM with K light chain specifically recognises PAPP-A from human, chimpanzee and rhesus primates.

The third monoclonal antibody—Clone 5-62, isotyped as $IgG_1$ with K light chains with an affinity constant of $2.65 \times 10^{-9}$ reacts specifically with human and chimpanzee PAPP-A but not with rhesus PAPP-A.

The fourth monoclonal antibody—Clone 18-9, isotyped as IgG with K light chains, reacts specifically with human and chimpanzee PAPP-A but not with rhesus PAPP-A.

The fifth monoclonal antibody—Clone 41.1, has yet to be isotyped and characterised.

The advantages conferred by the development of monoclonal antibodies to PAPP-A are that they are specific for a distinct epitope. This specificity allows the development of an assay with increased sensitivity and reliability. This increased sensitivity permits the detection of PAPP-A in the circulation within the first six weeks of normal pregnancy and depressed levels in abnormal pregnancies.

The use of monoclonal antibodies also permits the development of immunoassays which are independent of labelled antigen (PAPP-A). The term "immunoassays", as used herein, includes any method for PAPP-A detection mediated by the use of antibodies (classes IgG, IgA, IgD, IgE or IgM) or derivatives thereof (including Fab and F(ab)$_2$ fragments). Antibodies may be polyclonal or monoclonal, and may be generated by active immunisation of a host animal (including mouse, rat, guinea pig, rabbit, sheep, horse, donkey or other mammalian species), hybridoma technology and/or molecular biology for production of recombinant antibodies. Quantitative and qualitative PAPP-A detection may be achieved in liquid and/or solid phase and, in addition to immunoassays, includes in situ hybridisation and immunohistochemistry, by way of example.

Monoclonal antibodies also allow the development of sandwich assays with greater amplification potential. The single epitope specificity of the antibodies permits the detection of PAPP-A active sites and, therefore, quantification of bio-active PAPP-A.

According to a sixth aspect of the present invention, there is provided a method for the detection of PAPP-A in a sample using a monoclonal antibody of the fifth aspect to detect PAPP-A. Typically, the method comprises the steps of:-
 (i) contacting the sample with a PAPP-A capture phase which consists of one or more of the following:
  (a) monoclonal PAPP-A antibody;
  (b) polyclonal PAPP-A antibody;
  (c) immobilised heparin;
  (d) immobilised divalent metal cations (Cu++, Zn++, Co++, Ni++);
  (e) immobilized lectins (Concanavalin A, *Helix pomatia*, *Lens culinaris*, *Limulus polyphemus*, phytohaemaglutinin, *Ricinus communis*, Wheat germ, or others with equivalent specificities), and,
  (f) other specific (such as receptors) or non-specific ligands (such as dyes) with which PAPP-A has an affinity.
 (ii) contacting the immobilised or captured PAPP-A sample with a monoclonal antibody, of the fifth aspect of the invention, labelled with a detectable marker;
 (iii) incubating the sample and the labelled antibody to permit the labelled antibody to bind to any PAPP-A in the sample and;
 (iv) detecting the labelled antibody.

Typical methods include enzyme immunoassays (EIAs) or immunoradiometric assay (IRMA) formats.

According to a seventh aspect of the present invention there is provided a kit for the detection of PAPP-A in a sample which kit comprises:
at least one monoclonal antibody according to the fifth aspect of the present invention together with a positive and/or negative control. The PAPP-A assay kit, developed for manual and/or automated application, is not limited to human application. Selection of appropriate polyclonal-monoclonal PAPP-A antibody combination can extend application to sub-human primates.

The ability to produce large quantities of recombinant PAPP-A or variants thereof permits use as a medicament for the treatment of pregnant women with low or zero PAPP-A levels in order to increase the likelihood of the pregnancy proceeding successfully to term.

According to an eighth aspect of the present invention, there is provided the use of PAPP-A as a medicament together with a pharmaceutically acceptable excipient to treat a pregnant patient exhibiting the absence of or low levels of PAPP-A.

Formulation of PAPP-A for this purpose with standard carriers, excipients and diluents is performed in accordance with standard pharmaceutical techniques.

According to a ninth aspect of the present invention there is provided a medicament comprising an effective amount of PAPP-A together with a pharmaceutically acceptable carrier, diluent or excipient.

According to tenth aspect of the present invention, there is provided the use of PAPP-A as a target for immunological contraception. Immunological fertility regulation may be achieved by active vaccination against intact PAPP-A or fragments thereof. Active vaccination may be achieved by any of the accepted oral, mucosal or subcutaneous routes (of antigen administration) used to induce an immune response in humans. The PAPP-A antigen may be chemically modified, genetically engineered or the genome inserted into a vector to enhance immungenecity when expressed in the host.

Administration of PAPP-A antibodies (or fragments thereof) may be applied for fertility regulation by passive immunisation or for immunolocalisation and/or immunoneutralisation of trophoblastic tumors or management of extrauterine pregnancies. Antibody administration can be achieved by any of the procedures outlined for PAPP-A antigen administration.

According to the eleventh aspect of the present invention, there is provided the use of PAPP-A (polyclonal and monoclonal) antibodies for isolation of trophoblast cells from systemic maternal circulation or reproductive tract (vaginal cavity, cervical canal, cervical os). The isolated trophoblast cells may be cultured and applied for prenatal fetal karyotyping.

According to the twelfth aspect of the present invention, there is provided the use of PAPP-A immunodetection to discriminate between normal and abnormal pregnancies. Abnormal pregnancies include multiple gestations (more than one fetus), extra-uterine implantation, anembryonic pregnancies, death in utero, incomplete miscarriage, spontaneous abortion, fetal malformations and aneuploidies, as examples. Quantitative or qualitative PAPP-A immunodetection may be performed on maternal biological fluids, such as blood. Blood may be collected by routine venepuncture, finger pricking or by any accepted medical procedure. The blood may be anticoagulated or coagulated, to permit the removal of supernatant for PAPP-A analysis. The blood may be stored frozen or dried onto an inert absorptive medium, such as filter paper, for transportation, subsequent extraction and analysis.

According to the thirteenth aspect of the present invention, there is provided the use of PAPP-A immunodetection in female biological fluids, such as ovarian follicular fluid and reproductive tract secretions, to assess folliculogenesis, granulosa cell status and ovulation.

According to the fourteenth aspect of the present invention, there is provided the use of PAPP-A immunodetection for diagnosis and management of gestational trophoblastic disease (GTD). In hydatidiform mole, a benign GTD exhibits a molar expression ratio of PAPP-A to hCG (or free b-subunit) which is indistinguishable from that observed in normal pregnancy. As the GTD transforms into the more aggressive and invasive choriocarcinoma, the molar expression ratio of PAPP-A to hCG (or free b-subunit) decreases, that is hCG (or free b-subunit) expression is maintained or increased, whereas, PAPP-A expression is downregulated. This trophoblast antigen expression ratio can be applied as an algorithm for diagnosis and management of GTD.

According to a fifteenth aspect of the invention, PAPP-A antibodies are used for the immuno-treatment of trophoblastic tumors.

According to a sixteenth aspect of the present invention, there is provided the use of PAPP-A immunodetection in male reproductive tract secretions, such as seminal plasma and prostatic fluid, to assess the clinical state of male accessory glands, such as prostate gland, of the reproductive tract.

According to a seventeenth aspect of the present invention, there is provided the use of PAPP-A immunodetection for specific discrimination of pregnancies carrying Trisomy 21 (Down Syndrome) fetuses from normal and abnormal pregnancies. Although both hCG (and free b-subunit) and PAPP-A are trophoblast proteins, in this particular clinical situation their respective expression rates are discordant. Whereas PAPP-A expression is downregulated, hCG (and free b-subunit) expression is upregulated. Therefore, the molar expression of PAPP-A to hCG (or free b-subunit) can be applied as an algorithm for prenatal screening of Down Syndrome pregnancies in early gestation.

BRIEF DESCRIPTION OF THE DRAWINGS

The invention will now be described with reference to the following drawings:

FIG. 1 The N-terminal amino acid sequence of PAPP-A.

BEST MODE FOR CARRYING OUT THE INVENTION

Figure 2:
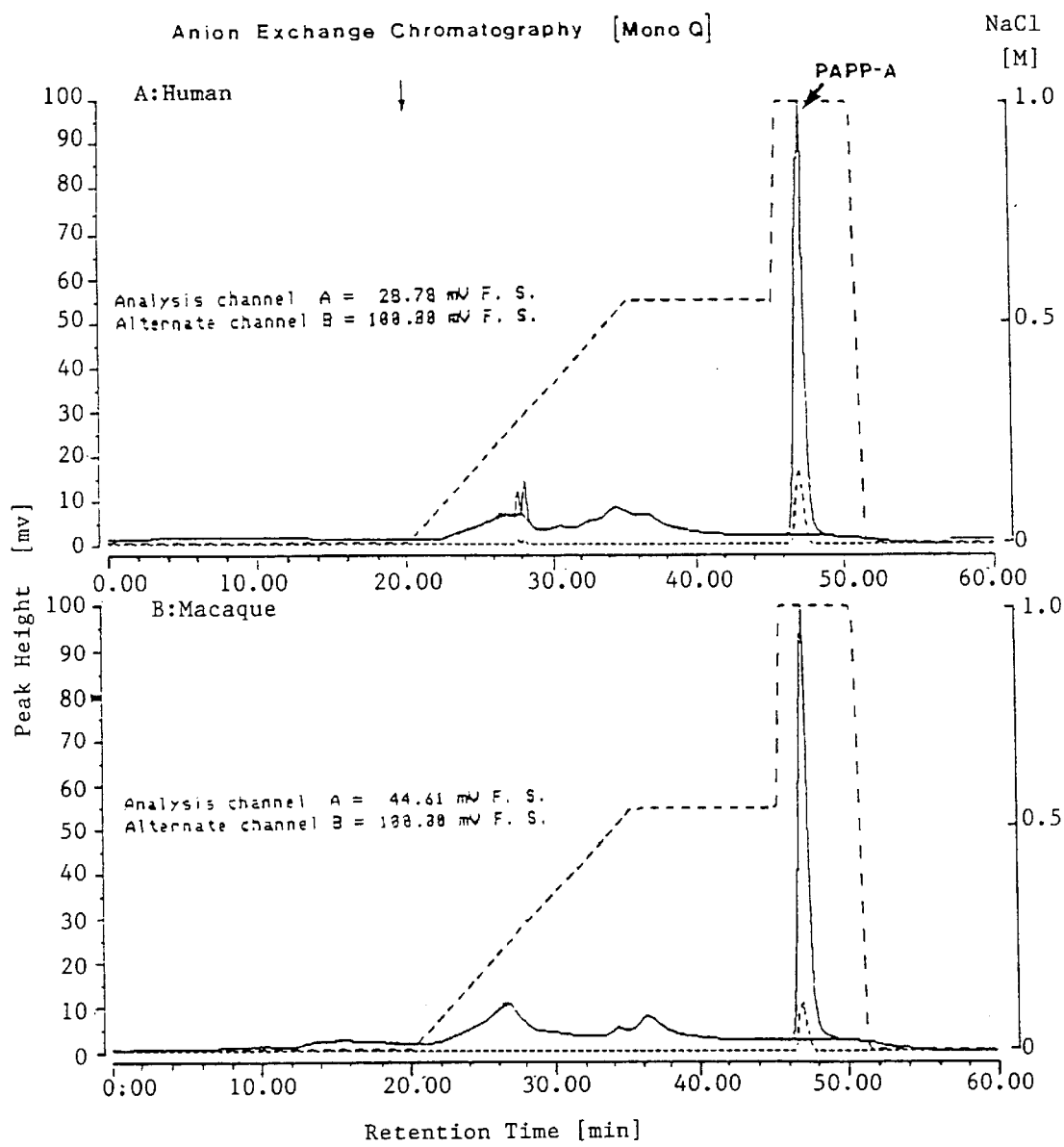
FIG. 2 Anion exchange on Mono Q. Purification of primate (human, A; macaque, B) PAPP-A by high pressure liquid chromatography anion exchange on Mono Q. Dashed lines represent increases in NaCl concentration to effect PAPP-A desorption (at 46–48 min).

Methods of recombinant PAPP-A production and preparation of variants are performed in accordance with standard techniques as taught, for instance, in Maniatis et al. (1984)[31] which is herein incorporated by reference. Formulation of PAPP-A medicaments is performed in accordance with standard pharmaceutical techniques.

Where recombinant techniques are used for the preparation of the protein of the invention, the protein can be prepared by constructing degenerate DNA probes coding for amino acid sequence of PAPP-A as described above and using these probes to isolate positive clones from c-DNA libraries according to standard techniques as found in text books such as Maniatis et al. (1984)[31]. These positive clones are then incorporated into appropriate vectors with expression cassettes according to standard techniques. These vectors are then used to transform host cells to allow the production of the recombinant PAPP-A protein.

The selection of appropriate vectors, hosts and expression strategies can be performed in accordance with standard techniques of molecular biology.

Suitable expression systems include, for instance, Chinese hamster ovary expression systems.

It will be readily apparent to a skilled artisan that where PAPP-A is produced recombinantly it may not be necessary to purify the protein before use. Recombinant production can be conducted in well-defined prokaryotic and eukaryotic hosts. Production in non-human systems yields the protein in a form at least substantially free of other human proteins.

The homologous polypeptides can be produced by conventional site-directed mutagenesis, which is one avenue for routinely identifying residues of the molecule that can be modified without rendering the resulting polypeptide biologically inactive, or by chemical synthesis.

Those variants which correspond to or comprise a portion of PAPP-A of the invention without being coincident with PAPP-A of the invention, within the scope of the invention, are those molecules which retain the immunogenic or biological activity of the native PAPP-A protein.

These variants may be prepared synthetically by peptide synthesis techniques, recombinantly or by cleavage from an isolated protein of the invention.

Methods of isolating, characterising and cloning polynucleotides encoding PAPP-A using probes constructed from the N-terminal amino acid sequence are performed in accordance with standard techniques as taught, for instance, in Maniatis et al (1982)[31].

Isolation and Purification of PAPP-A

The protocol consists of five chromatographic procedures and is applicable to human and non-human PAPP-A species. The protocol can be used to isolate PAPP-A from any biological fluid, culture medium or tissue extract.

1. Positive Affinity Chromatography on Heparin-Sepharose:

The column was equilibrated with aqueous buffers, such as 50 mM Tris-HCl, pH 7.4–7.8, containing 150 mM NaCl (TBS—0.15 M NaCl). Sample application (1 ml/min) resulted in only 11.3% of applied serum proteins being bound to the matrix. The remaining proteins do not interact with heparin and are easily removed from PAPP-A. By increasing the ionic strength of equilibration buffer to BS—0.3M NaCl, the low affinity heparin interaction was reduced and only 0.5% of applied proteins were retained by the ligand (heparin). Although PAPP-A recovery was 100%, the yield was 39% for a purification factor of 486.

Heparin-PAPP-A interaction is heterogeneous, with minor amounts of PAPP-A not interacting with heparin (Sinosich 1985)[27]. Although the significance of this heterogeneity is uncertain, it is clearly not related to heparin. Therefore, the heterogeneity resides with PAPP-A and may be related to PAPP-A isoforms or metabolic, clearance, and, hence, provide a distinction between functional and inactive PAPP-A.

Desorption of matrix bound PAPP-A was achieved with application of high ionic strength buffers, such as TBS containing 0.6M NaCl or greater (up to 2.0M NaCl). PAPP-A elutes as a sharp peak and is concentrated into 3 or 4 fractions, dependent on column size and fraction volume. Desorption may also be achieved by applying the heparin antagonist, protamine sulphate, but matrix regeneration is more complex.

2. Size Fractionation:

PAPP-A containing fractions were pooled (36 ml) and applied onto a 5×90 cm column (Vol=1.71l) packed with gel filtration matrix Ultragel AcA34 or AcA22 or equivalent. PAPP-A containing fractions were pooled and dialysed against 20 mM TBS, containing 10 mM NaCl, pH 7.4–7.8. PAPP-A recovery for this procedure was 98.8% with an overall purification factor of 827.

3. Anion Exchange (Mono O):

The dialysed PAPP-A pool (110 ml) from size fractionation was applied onto a 10 ml anion exchange column, such as Mono Q, by high pressure liquid chromatography. The PAPP-A containing pool from size fractionation was applied in 10 ml aliquots at 1 ml/min. After 20 min., buffer ionic strength was increased to TBS-0.5M NaCl by a gradual linearly increasing concentration gradient in NaCl. This removed low affinity interactions. The high affinity PAPP-A interaction was dissociated with a stepwise increase in NaCl concentration to TBS-1M NaCl (FIG. 2).

4. Negative Immunoaffinity Chromatography:

Rabbit antibodies against serum proteins, heparin binding serum and tissue proteins were immobilised onto inert particles such as CNBr-Sepharose. PAPP-A containing fractions (25 ml) from step 3 (above) were repeatedly passed over this matrix to remove any contaminants.

5. Positive Affinitive Chromatography:

This is optional, but provides an easy means of concentrating PAPP-A from larger into smaller volumes prior to aliquotting and storage. PAPP-A pool (90 ml), from step 4 was applied onto a 120 ml Heparin-Sepharose column. Matrix bound PAPP-A is desorbed with TBS-1M NaCl for a final PAPP-A yield of up to 22%, for an overall purification factor of 1483.

6. The purity of PAPP-A preparation was assessed and confirmed by:

i) SDS-PAGE analysis (Sinosich et al., 1990)[28]

ii) radioimmunoassay (Sinosich and Zakher, 1991[29]; Sinosich et al. 1982[2], 1984[6]) and iii) $NH_2$-terminal amino acid sequencing.

The $NH_2$-terminal amino acid sequence for PAPP-A was sequenced by the School of Biological Sciences, Macquarie University according to standard techniques and was determined to be:

Glu-Ala-Arg-Gly-Ala-Pro-Glu-Glu-Pro-Ser-Pro-Pro-Ser [SEQ ID NO:1]

As there is only one $NH_2$-terminal amino acid sequence detected, this indicates both that PAPP-A preparation is free of contamination with other proteins, and PAPP-A subunits are identical.

As this sequence is unique to PAPP-A, immunodetection of PAPP-A means the detection of a protein or proteins containing this $NH_2$ terminal amino acid sequence.

Monoclonal Production

Immunisation:

Pure PAPP-A, isolated from pooled late pregnancy serum was used to immunise BALB/c mice by two protocols.

PAPP-A (30 μg) in 0.05M sodium phosphate buffer, pH 7.4, containing 150 mM NaCl (50 μl; PBS) was emulsified in 50 μl Complete Freund's Adjuvant (CFA) and injected into the footpads of mice. Fourteen (14) days later, a booster dose of 65 μg PAPP-A/100 μl PBS was injected into the thigh muscle of Mouse 1. This mouse was sacrificed 5 days later for hybridoma cell fusion.

Mouse 2 was subcutaneously immunised with 130 μg PAPP-A in CFA, followed, three weeks later, with an intraperitoneal injection of 150 μg PAPP-A in Incomplete Freunds Adjuvant (ICA). One week later the mouse was boosted with an intravenous injection of 65 μg PAPP-A and the animal sacrificed five days later.

Hybridomas were prepared by fusing splenocytes and inguinal lymph node cells with X63 Ag 8.6.5.3. myeloma cells (Gaefee et al. 1977) and cultured in HAT medium. Once established, the selected hybridomas were cultured in aminopterin-free HT medium. Antibody production was monitored by enzyme immunoassay (EIA) and antibody producing cells were cloned by limiting dilution and expanded. Hybridoma cells were injected intraperitoneally into BALB/c mice, primed with 2,6,10,14-tetramethyl pentadecane (pristene; Sigma, Sydney) to produce ascitic fluid.

Immunoassays:

Screening for antibody production was achieved by a crude EIA. Flat bottom Maxisorp Immunoplates (Nunc) were coated overnight (12–18h), at 4 C, with heparin-binding proteins (37.5 mg PAPP-A/well; See Isolation 1) extracted from pooled pregnancy serum (38 weeks gestation: n 250). The plates were washed once with 50 mM sodium phosphate buffer, pH 7.4, containing 0.15M NaCl (PBS). Unreacted protein binding sites were blocked, by incubating for 90 min at room temperature (RT; 21–24 C), with PBS containing 0.1% bovine serum albumin (BSA) and 0.2% $H_2O_2$. Plates were washed (X3) with PBS containing 0.1% BSA and 0.1% Tween-20 (T-PBS). Spent hybridoma culture media (250 μl) was incubated for 2 hr at room temperature after which the plates were washed (X3) with T-PBS and incubated, for 1 h at room temperature, with horseradish peroxidase conjugated rabbit anti-mouse IgG (200 μl/well; Dakopatts, Sydney), diluted 1/5000 in T-PBS. The plates were washed (X3) with T-PBS and incubated in the dark, for 15 min at RT, with substrate (200 μl/well; O-phenylenediamine (OPD), 0.67 mg/ml), in 0.1M citric acid phosphate buffer, pH 5.0, containing 0.012% $H_2O_2$. The reaction was terminated by addition of 1M sulphuric acid (100 μl/well) and absorbance measured at 490 nm on a microplate reader (Biotek).

Positive hybridoma media were screened by PAPP-A RIA. The final incubation volume (200 μl) consisted of hybridoma medium (100 μl) and tracer ($^{125}$I-PAPP-A; 50 000 cpm/100 μl). After overnight incubation at room temperature, pooled serum (50 μl) obtained from normal human males was added to each tube and antibody bound tracer was precipitated by the second antibody-polyethylene glycol method (Sinosich et al., 1982)[9]. The supernatant was aspirated and precipitated radioactivity measured by a multichannel gamma-counter (NE, Sydney).

Murine immunoglobulins were typed by EIA using a panel of rabbit anti-mouse immunoglobulins ($IgG_1$, $IgG_{2a}$, $IgG_{2b}$, $IgG_3$, IgM, IgA, K light Chain, K Chain; Biorad Laboratories, Sydney).

A rabbit polyclonal antibody was prepared by repeated intramuscular injections of pure PAPP-A (100 μg). After a positive test bleed was obtained, the animal was boosted with 100 μg PAPP-A administered subcutaneously. Antibody responses were monitored by RIA on blood samples obtained from the marginal ear vein.

Biotinylation of Immunoglobulins:

Anti-PAPP-A IgG molecules were isolated from polyclonal and monoclonal antisera by affinity chromatography on a 3 ml column of Protein-A Sepharose (Pharmacia, Sydney), as per manufacturer's instructions. Matrix bound proteins were desorbed with 0.2M glycine-HCl, pH 3.0, and dialysed (3X20 volumes) against PBS. Approximately 1 mg of polyclonal IgG was recovered per ml of rabbit serum and 2.5 mg of IgG was recovered from 50 ml of culture supernate. Each preparation (1 mg/ml) was biotinylated with the long-chain derivative of N-hydroxysuccinimido-biotin (NHS-LC-biotin), as per manufacturer's instructions (Amersham, Sydney). After 1 hr incubation at room temperature, unconjugated biotin was separated from the protein on a PD10 (Sephadex G-25M) column (Pharmacia) developed with PBS.

Development of PAPP-A Enzymeimmunoassay (EIA):

Micro-ELISA (96 well) plates were coated, overnight at 4 C, with polyclonal rabbit anti-PAPP-A IgG in PBS. After coating, the plates were washed with PBS and unreacted sites blocked (as detailed above). Assay reaction volume was 200 μl with all samples/standards assayed in duplicate. Serum obtained from women (n>250) at advance stages of gestation (38 weeks) was pooled (LPS) and designated as 100 IU PAPP-A/L. The pooled LPS was serially diluted (1/16-1/8196) to prepare a standard curve, 12.2-6246 mIU/L).

Affinity Immunoelectrophoresis (AIE):

Pooled late pregnancy serum (38 weeks gestation; LPS) was incubated, overnight at room temperature, with media (control) or monoclonal antibody (5-62, 27-66, 25-1, 18-9) in a 1:1 ratio (v/v). An aliquot (10 μl) was electrophoresed in the first dimension, in the absence and presence of heparin (+H; 20 units/ml gel), at 10 V/cm until the bromophenol blue marker migrated 3 cm. The gel was sliced and migrated in the second dimension into gel containing polyclonal rabbit anti-PAPP-A antibodies (Dakopatts) at 1/150 dilution. Second dimensional electrophoresis (at 2.5 V/cm) was performed overnight and the agarose gels processed for visualisation. Changes in migration distance (mm) were expressed as percentage of control value[27].

Immunohistochemistry (ICC):

Term human placenta, obtained by caesarean section, was sliced and fixed in phosphate buffered formalin (4%), pH 7.4, for 24 h at 4 C. The tissue was then washed in phosphate buffered saline, pH 7.4, for 24 h and processed by standard histological techniques. Sections (5 μm) were deparaffinised and processed for immunohistochemistry with polyclonal rabbit anti-chorionic gonadotrophin (Dakopatts),—PAPP-A (Sinosich et al. 1987) and monoclonal anti-PAPP-A (clone 25-1). Visualisation was achieved by enzyme bridge immunoperoxidase system using DAB as substrate. Negative controls included non-immune rabbit serum, mouse serum and culture media.

RESULTS

A total of five (5) anti-PAPP-A clones were obtained; 1) clone 25-1, isotyped as $IgG_1$ with K chain, 2) clone 27-66, isotyped as IgM with K chain, 3) clone 5-62, isotyped as $IgG_1$ with K chain, 4) clone 18-9, isotyped as IgG with K chain, and, 5) clone 41-1, which has yet to be characterised. By enzyme immunoassay, none of these antibodies reacted with immobilised heparin-Sepharose binding proteins extracted from normal male serum. The affinity constants ($M^{-1}$) for clones 25-1 and 5-62 were $1.26 \times 10^{-9}$ and $2.65 \times 10^{-9}$, respectively.

Figure 3:
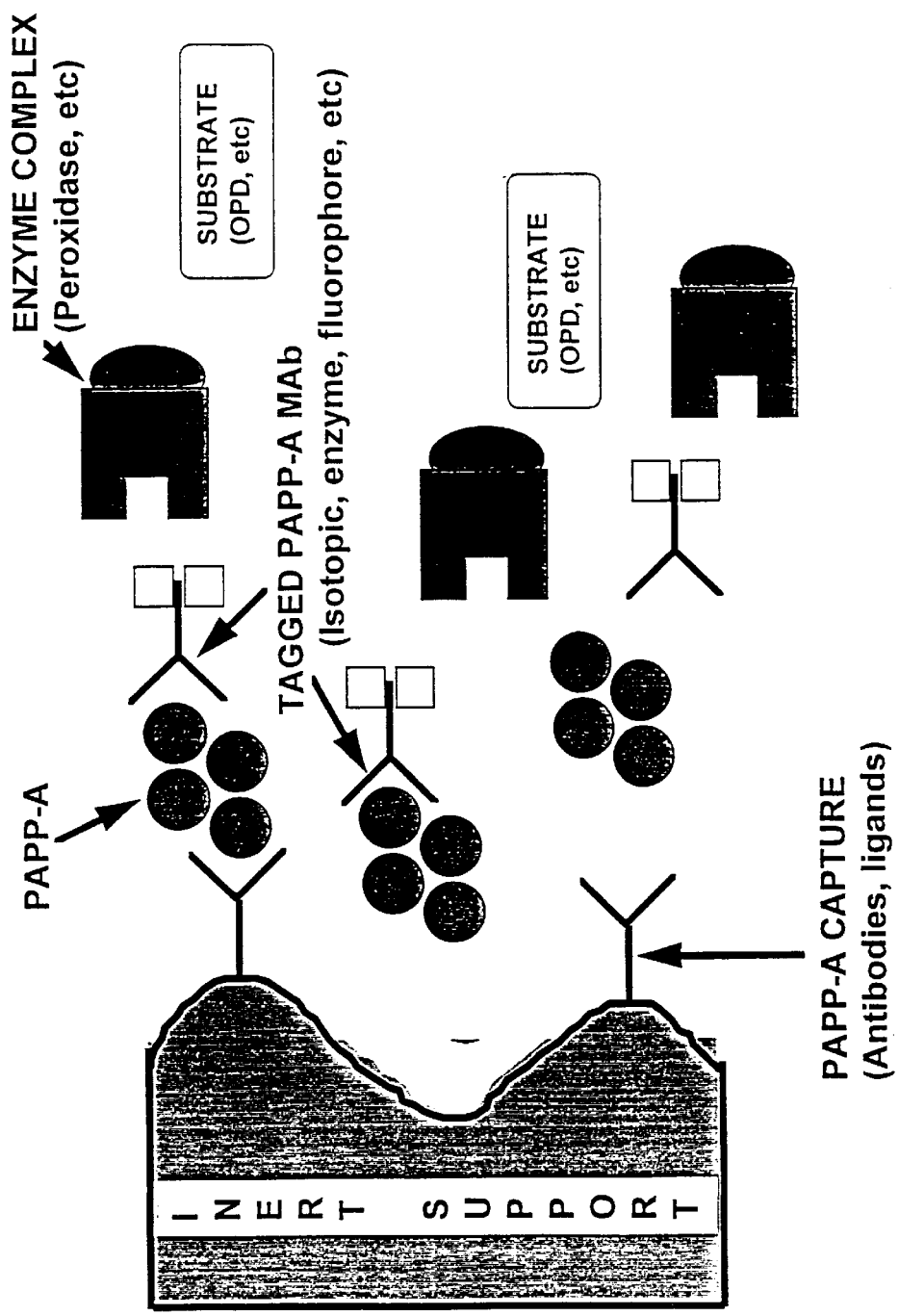
FIG. 3 Assay protocol for PAPP-A quantification consists of a capture phase immobilized on an inert support and a monoclonal antibody for quantification. The monoclonal antibody may be tagged or visualized with a secondary antibody. The latter option enhances signal amplification and assay sensitivity.

A sandwich enzyme immunoassay was developed using immobilised rabbit polyclonal anti-PAPP-A immunoglobulins as capture phase and clone 25-1 immunoglobulins for PAPP-A quantification (FIG. 3). This assay protocol is applicable to other PAPP-A monoclonal antibodies, but only clone 25-1 will be detailed.

Capture phase may include:
1) polyclonal PAPP-A antibody,
2) monoclonal PAPP-A antibody,
3) ligands, such as heparin, immobilised metal (zinc, copper, cobalt, nickel) cations and lectins (Con A, PHA) as detailed before,
4) specific, such as receptors, and non-specific, such as dyes, ligands for PAPP-A.

Figure 4:
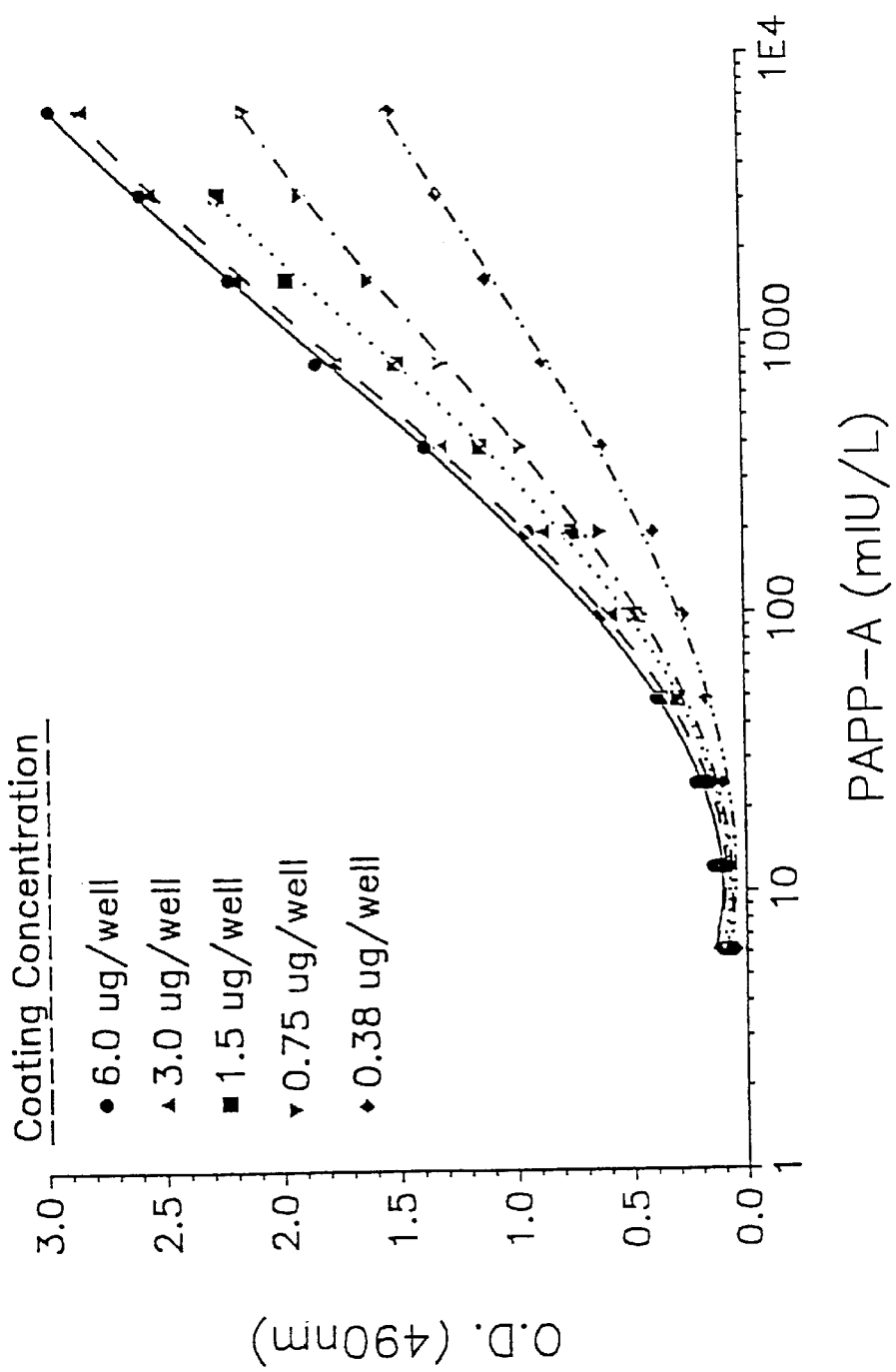
FIG. 4 Influence of capture antibody concentration on PAPP-A standard curves.

Coating concentrations of rabbit immunoglobulins ranged from 0.38–6.0 µg/well. At concentrations in excess of 1.5 µg/well, the increase in absorbance (at 490 nm) was insignificant. Thus, the EIA was developed on a coating concentration of 1.5 µg rabbit immunoglobulins per well. (See FIG. 4).

Figure 5:
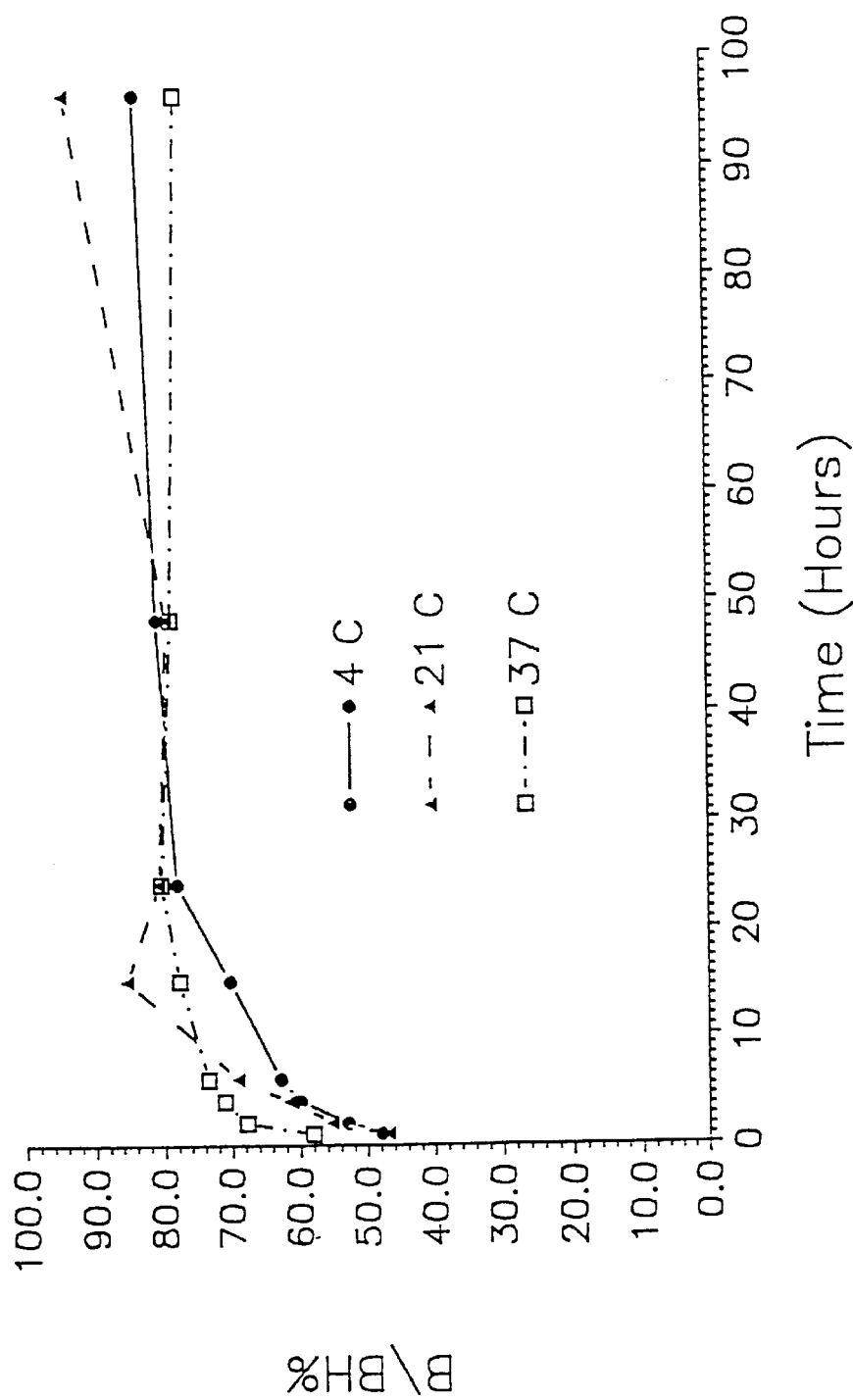
FIG. 5 Influence of temperature on the binding equilibrium of immobilised immunoglobulin at 4° C., room temperature and 37° C., Maximal PAPP-A capture was achieved after overnight incubation (15 hours).

The influence of time and temperature on PAPP-A capture by immobilised polyclonal anti-PAPP-A immunoglobulins is shown in FIG. 5. Independent of PAPP-A doses (0-6250 mIU/L) and temperature (4° C.; room temperature, 19–23° C.; 37° C.), binding equilibrium was attained by the capture antibody within 24 h. At room temperature or 37° C., maximal PAPP-A capture was achieved after overnight incubation (15 h) and these conditions (overnight incubation at room temperature) were selected for assay development.

Figure 6:
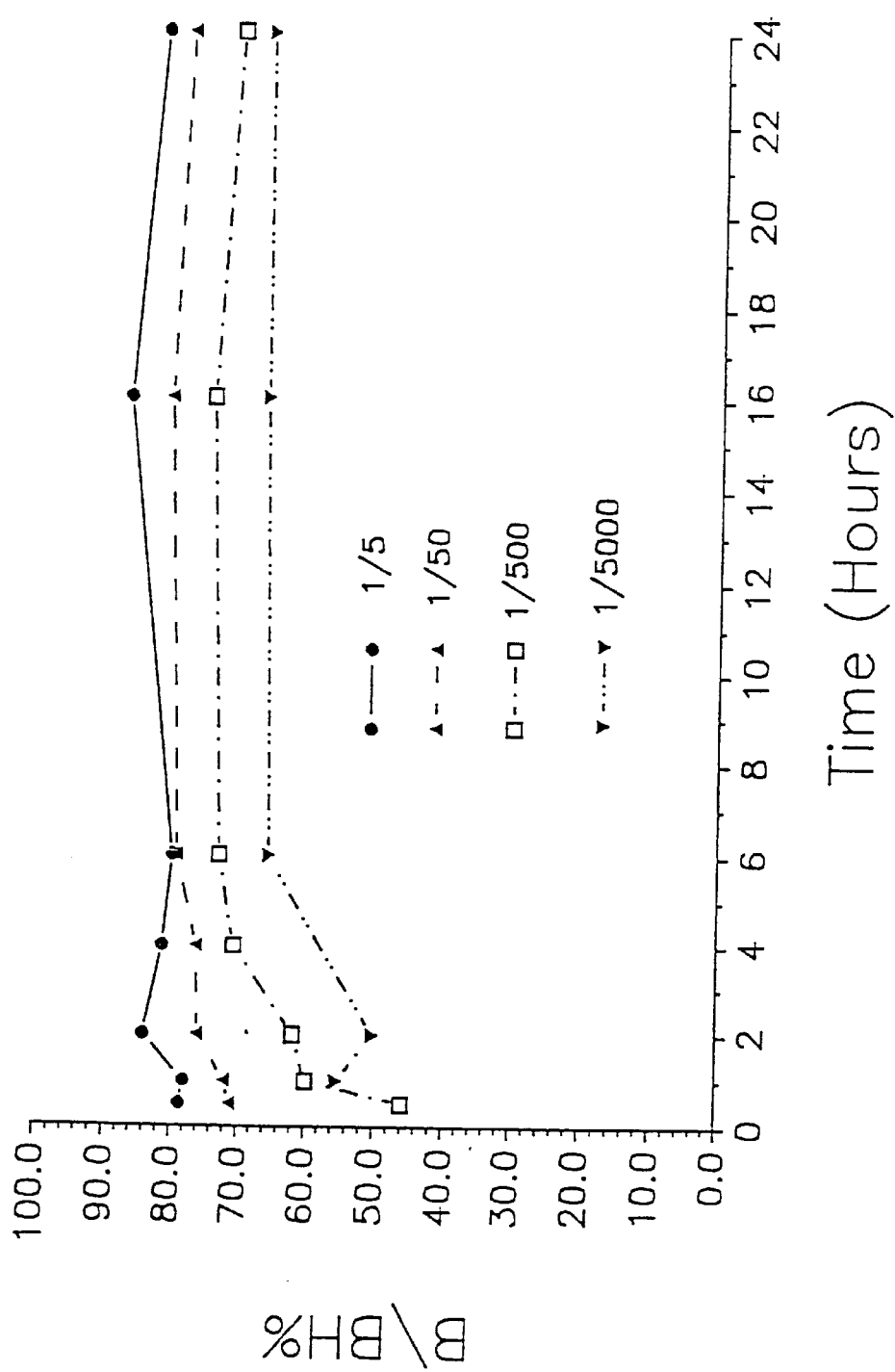
FIG. 6 Binding equilibrium of monoclonal antibody clone 25-1 at various concentrations. Binding equilibrium was achieved by 4 hours at room temperature.
Figure 7:
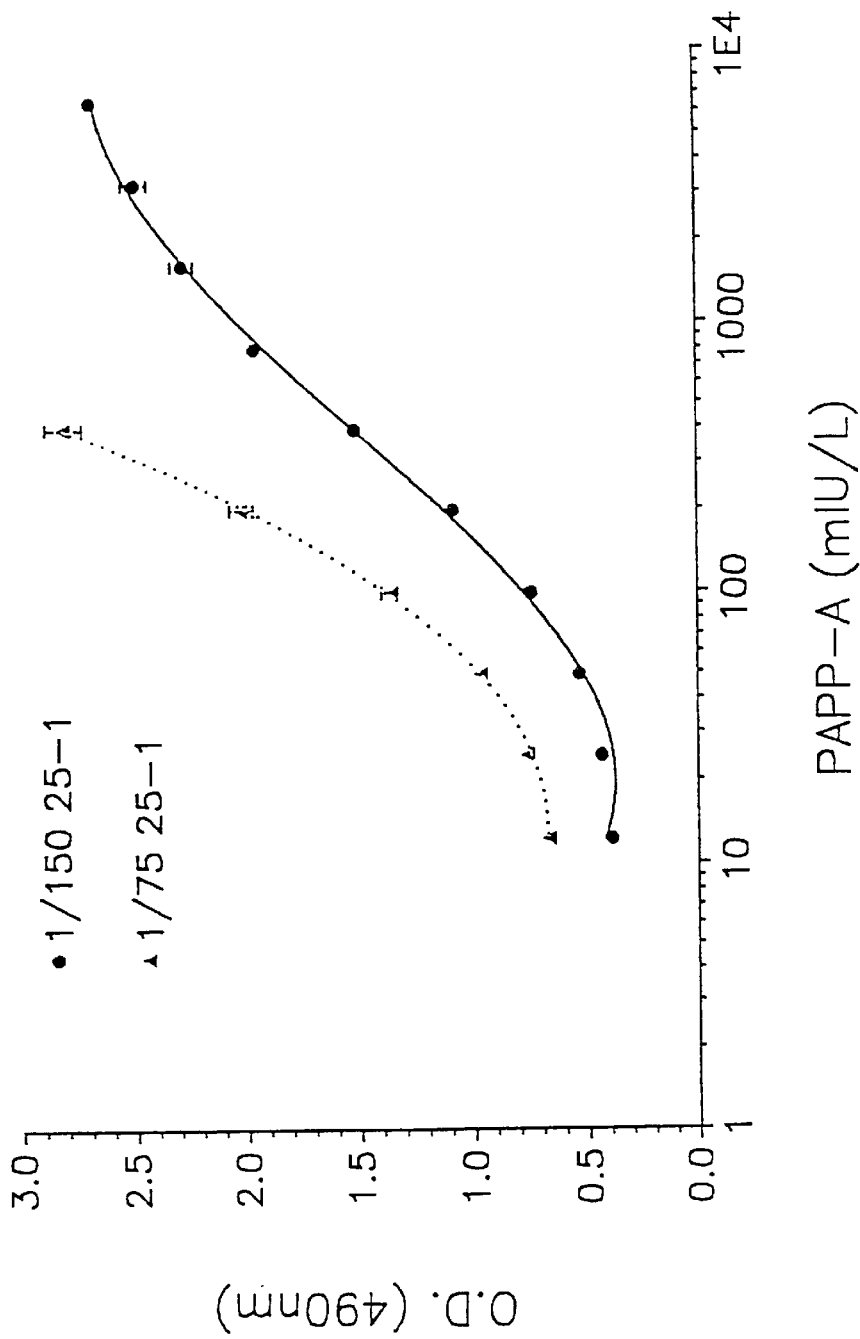
FIG. 7 Standard curves for PAPP-A dose response at two dilutions for clone 25-1.

Using biotinylated 25-1 antibody, at varied dilutions (1/5, 1/50, 1/500, 1/5000), binding equilibrium was achieved (at room temperature) by 4 h. (FIG. 6) The time required to attain equilibrium was inversely proportional to antibody concentration, with maximal binding being achieved within 30 min in excess antibody (1/5 dilution). Using these conditions (4 h at room temperature), FIG. 7 shows typical PAPP-A dose-response curves at two dilutions (1/75, 1/150) of clone 25-1. For greater sensitivity the monoclonal antibody was diluted 1/75, but for routine assays not requiring enhanced sensitivity the antibody was diluted 1/150. Assay detection limit (n=20 replicates) was 21 mIU/L, with inter-assay precision of 6.2% and 10.5%. At PAPP-A doses of 100 and 1000 mIU/L and intra-assay precision was 9.2% (100 mIU/L) and 11.3% (1000 mIU/L), respectively. Total turn-around time for this assay was 24 hrs.

Specificity was assessed in two ways. Firstly, by incubating each monoclonal PAPP-A antibody with immobilised heparin-Sepharose binding proteins, extracted from normal male serum. No significant reaction was detected. Secondly, at a fixed dose of PAPP-A (390.4 mIU/L) various monoclonal and polyclonal antisera (1/100 dilution) were tested for competition against biotinylated PAPP-A monoclonal 5-62, 25-1 (Table 1) and 18-9 (not shown). Positive reactions (>20% suppression in absorbance) were demonstrated with polyclonal anti-human, anti-monkey (rhesus) PAPP-A and rabbit anti-human placenta antisera (Table 2). Positive controls included the same monoclonal antibody as the test, but in the non-biotinylated form. All of the other antisera (PZP, a2M, SP1, complement factors 3 and 4, etc. Table 2) yielded negative results. Since the monoclonal anti-PAPP-A antibodies did not inhibit each other, except in a positive (self-self) format, these monoclonals recognise distinct epitopes.

Figure 8:
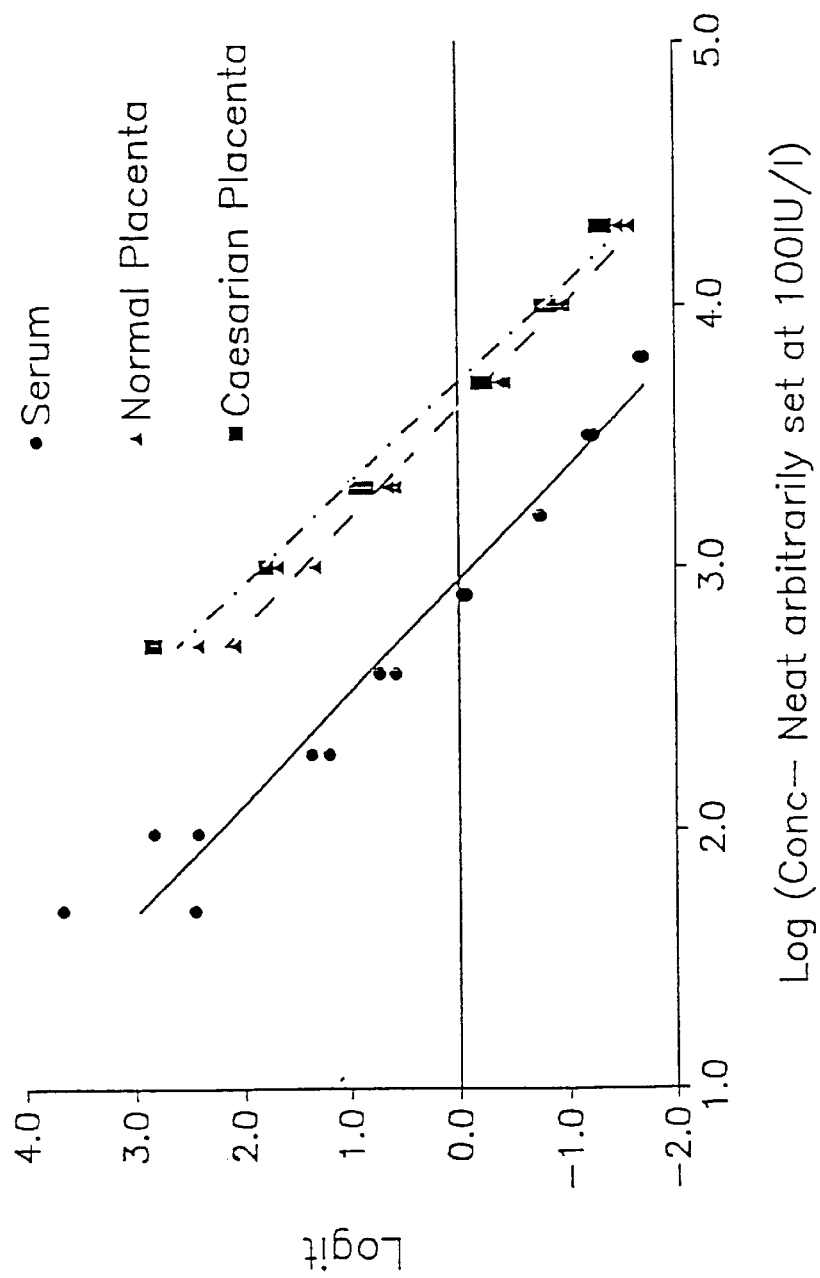
FIG. 8 Logit-log graphs for human serum and normal and caesarian placental homogenates assayed by RIA with clone 25-1. The results suggest parallelism between circulating and tissue PAPP-A.
Figure 9:
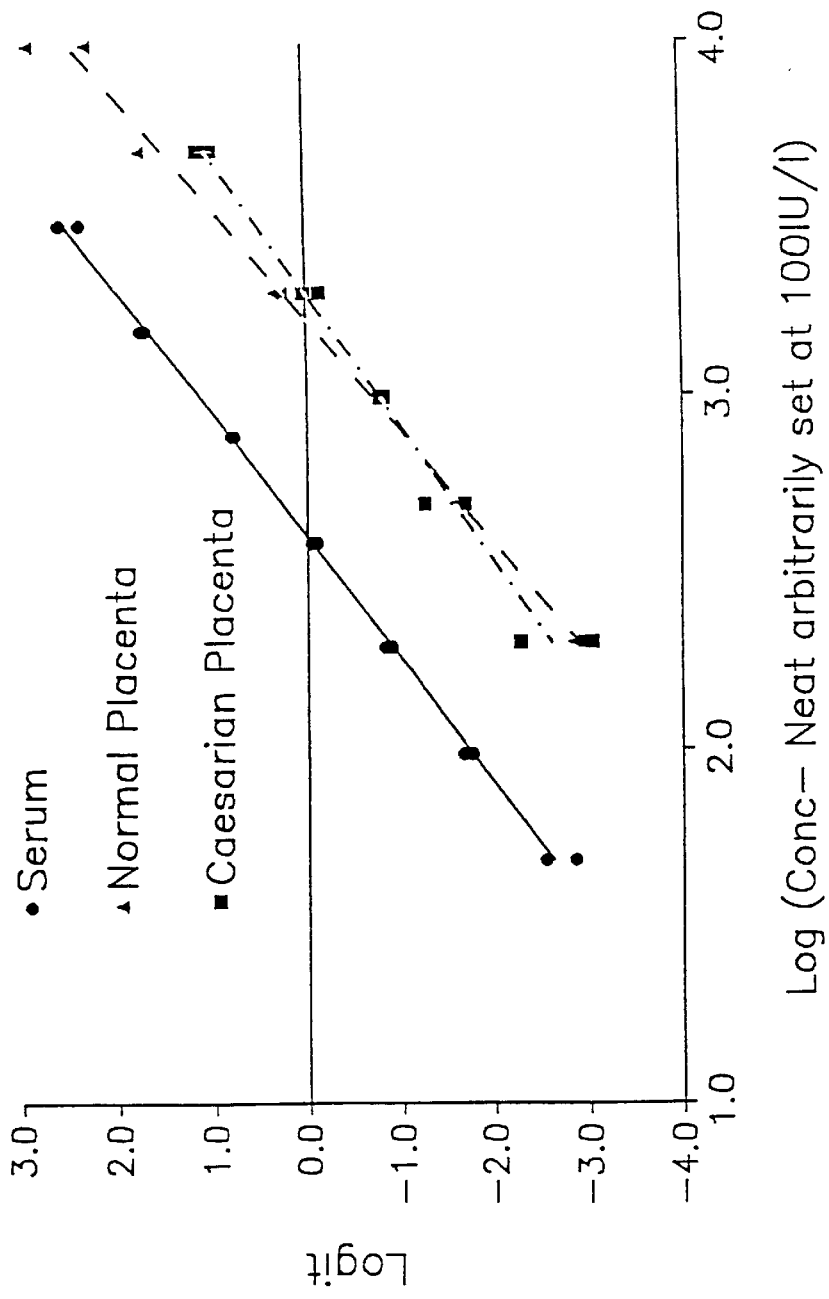
FIG. 9 Logit-log by graphs for human serum and normal and caesarean placental homogenates assayed by EIA with clone 25-1. The results again suggest parallelism between circulating and tissue PAPP-A.
Figure 10:
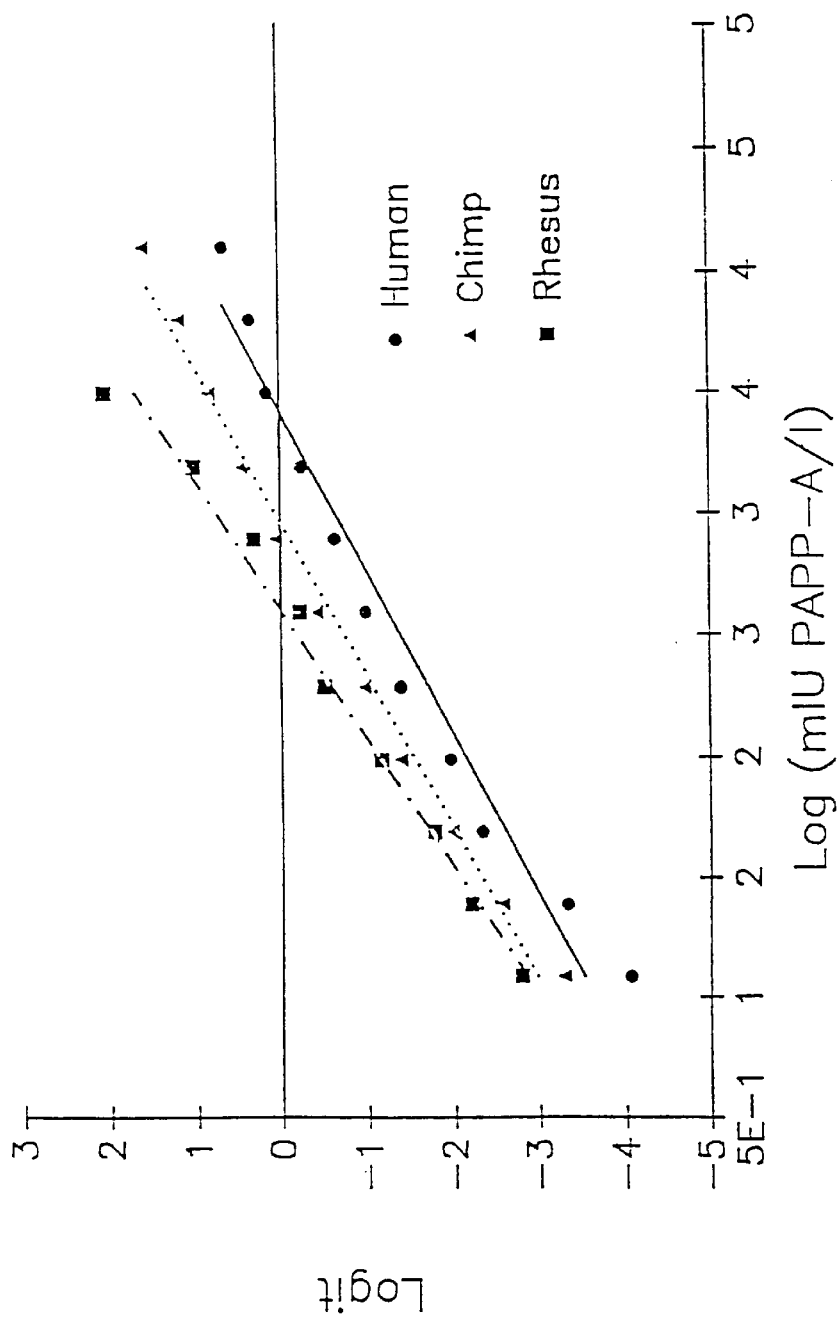
FIG. 10 Logit-log graphs for human, chimpanzee and rhesus placental homogenates assayed by EIA with clone 27-66. The results indicate that clone 27-66 equally reacts with PAPP-A from all three species.
Figure 11:
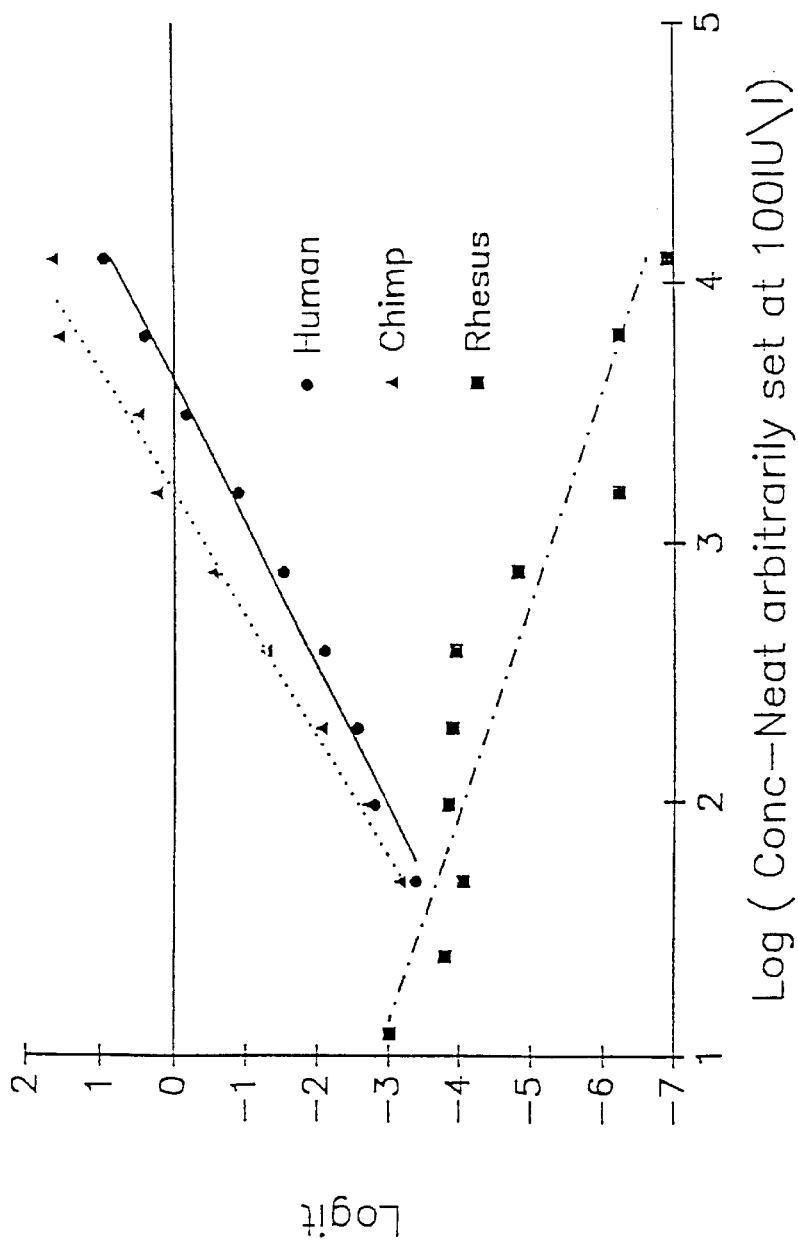
FIG. 11 Logit-log graphs for human, chimpanzee and rhesus placental homogenates assayed by EIA with clone 5-62. The results indicate that clone 5-62 reacts with PAPP-A from human and chimpanzee but not rhesus.
Figure 12:
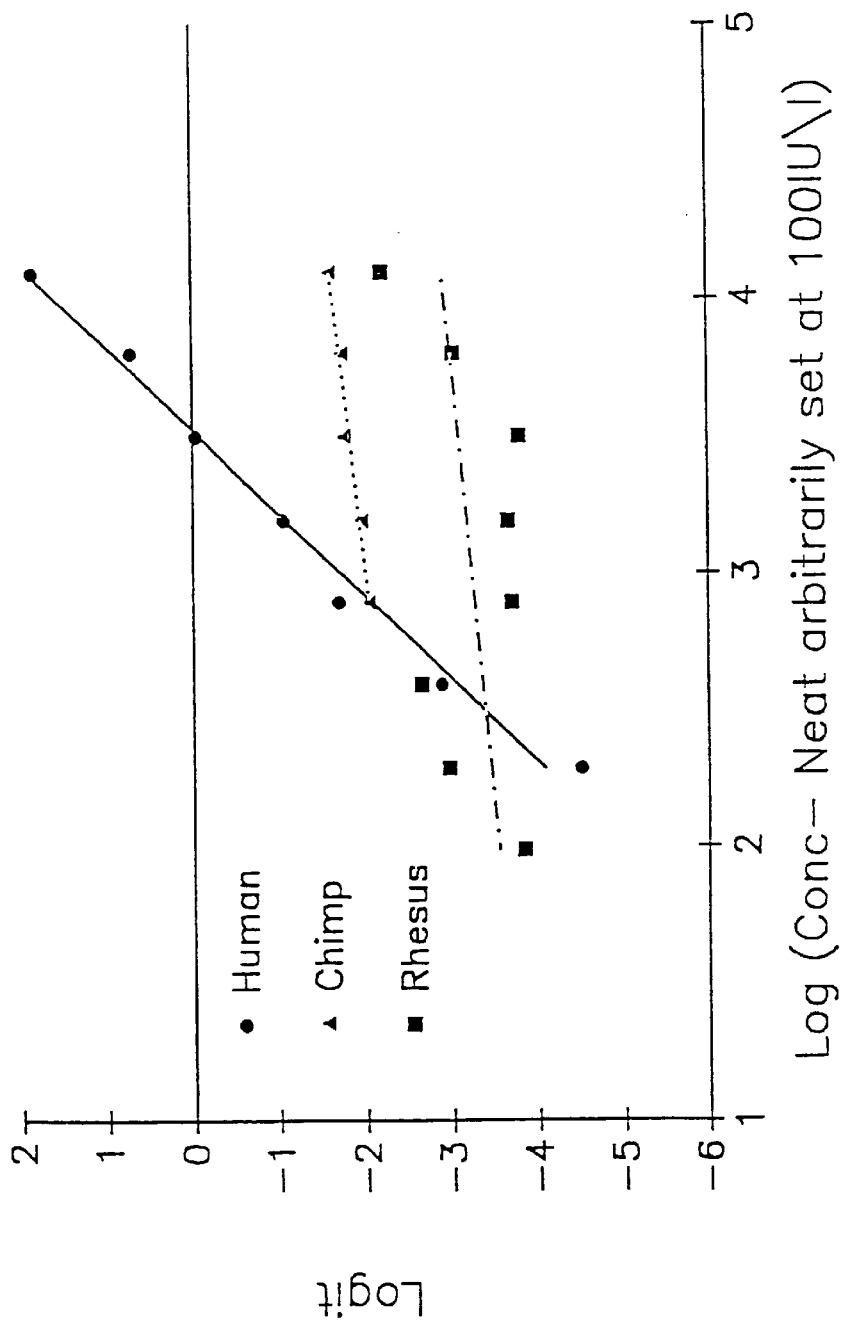
FIG. 12 Logit-log graphs for human, chimpanzee and rhesus placental homogenates assayed by EIA with clone 25-1. The results indicate that clone 25-1 reacts only with human PAPP-A.

Serially diluted late pregnancy serum, and extracts of placentae, delivered either by caesarean section or spontaneously per vagina, were analysed by RIA and EIA using clone 25-1 as primary antibody. Slopes of the logit-log regressed lines (FIGS. 8 & 9) suggests parallelism between circulating and tissue PAPP-A. However, comparison of dose-response for extracts of human, chimpanzee and rhesus placentae showed marked species dependent responses. Clone 27-66 did not distinguish between three primate PAPP-A species (FIG.10). Clones 5-62 and 18-9 (not shown) demonstrated parallel lines only between human (m=1.82) and chimpanzee (m=2.13) PAPP-A (FIG. 11). In contrast, clone 25-1 reacted only with human (m=3.32), but not with chimpanzee (m=0.36) or rhesus (m=0.31) PAPP-A (FIG. 12).

After incubation with a variety of glycosidases immunoreactivity of radiolabelled ($^{125}$I-) PAPP-A to the two IgG clones (25-1, 5-62) was unchanged. Incubation with a-glucosidase and neuraminidase caused a marked increase in NSB, so that it was not possible to determine the true Bo (%). By contrast, incubation of PAPP-A tracer with proteases (trypsin, elastase) markedly reduced PAPP-A immunoreactivity. These findings suggest the monoclonal antibodies recognise protide epitopes, rather than carbohydrate moieties.

By two dimensional immunoelectrophoresis, PAPP-A had a 2-electrophoretic mobility (39 mm). In the presence of IgG (5-62, 25-1, 18-9) and IgM (27-66 ) clones, PAPP-A mobility was reduced by 25.6% and 43.6%, respectively,. In the presence of heparin (20 units/ml gel), PAPP-A migration was increased by 33.3%. As none of the four clones inhibited the heparin-PAPP-A interaction, these epitopes are not associated with the heparin binding site of PAPP-A.

Immunohistochemical localisation of PAPP-A (clone 25-1) in human term placenta was limited to the syncytial layer. No PAPP-A immunoreactivity was detected in foetal or maternal blood vessels or villous stroma.

The monoclonal antibody is typically used for diagnostic or therapeutic purposes in unlabelled and/or labelled form. Typical labels include fluorescent, biotin, radioisotopic, chromogenic, chemiluminescent, electron dense, magnetic labels and enzyme labels, as examples. Labelling may also be achieved by means of a second antibody against the primary antibody with the second antibody being detectably labelled.

PAPP-A measurement in female (ovarian follicular fluid, cervical mucus) and male (seminal plasma, prostatic fluid) reproductive tract secretions can be of use to assess folliculogenesis, granulosa cell status, ovulation and pathology of the male accessory glands, such as prostate gland. Each fluid should be centrifuged to remove cells and the supernate stored at −20° C., until required for analysis. Cervical mucus should be extracted with 500 ul of assay buffer, centrifuged to remove cells and cellular debris, and supernate stored at −20° C. until required for analysis.

Blood, obtained by routine venepuncture, can be collected into anticoagulant free tubes or into anticoagulant (heparin, EDTA, citrate, as examples) containing tubes. In each case the sample should be centrifuged to separate the serum/plasma phase from blood cells. The supernate fluid is aspirated and stored at −20° C. until required for analysis.

In the case where trophoblast cells are to be isolated, anticoagulated (EDTA, citrate, heparin) maternal blood or vaginal fluid is washed with physiological buffers or culture media to remove the plasma. The sedimented cells are resuspended in buffer or culture media and incubated with one or more PAPP-A polyclonal or monoclonal antibodies (or their derivatives). These PAPP-A antibodies may be free or immobilised, for example on magnetised particles. The free PAPP-A antibodies can be removed with a capture phase, such as Protein-A Sepharose, secondary antibody immobilised on magnetic and non-magnetised particles. The isolated trophoblast cells can be used for fetal karyotype, fluorescent in situ hybridisation (FISH), molecular biology, cell culture and immunocytochemical studies.

Tissue, for cell culture and immunohistochemical analyses, can include any desired normal and pathological tissue. Cell isolation and tissue processing was achieved by standard protocols as detailed above.

Immunodetection of PAPP-A, in maternal blood, can be used to assess pregnancy wellbeing and as part of a prenatal biochemical screen to assess fetal development. In all adverse clinical situations, such as extra-uterine pregnancies, fetal death in utero, anembryonic pregnancy, incomplete abortion, spontaneous miscarriage, fetal malformation and/or aneuploidy (chromosomal abnormality), as examples, PAPP-A levels are depressed in maternal circulation. Although, in most of the pregnancy disorders, hCG (or free β-subunit) expression correlates with PAPP-A levels. In Trisomy 21 (Down Syndrome) hCG (or free β-subunit) expression is increased. Therefore, development and application of an algorithm which combines PAPP-A and hCG (or free β-subunit) measurements will permit discrimination of Trisomy 21 (Down Syndrome) from other pregnancy disorders. With a sensitive immunoassay, PAPP-A measurement can be established as an integral part of antenatal care in the first trimester of pregnancy.

In oncological situations, PAPP-A is expressed by tumor granulosa cells and gestational trophoblastic diseases (GTD). As the GTD becomes more aggressive and metastatic, PAPP-A expression is downregulated. By contrast, hCG and free β-subunit expression is upregulated. Again, application of a PAPP-A—hCG (or free β-subunit) algorithm enables discrimination between malignant and benign GTD.

INDUSTRIAL APPLICABILITY

In addition to the industrial applicability already indicated, it is envisaged that PAPP-A and PAPP-A variants can be used as a medicament to treat pregnant women exhibiting low levels of PAPP-A.

The amount of PAPP-A or variant required to produce a single dosage form will vary depending upon the condition to be treated, patient to be treated and the particular mode of administration. The specific dose level for any particular patient will depend upon a variety of factors including the activity of the molecule employed, the age, body weight, general health and diet of the patient, time of administration, route of administration, rate of excretion, drug combination and the severity of the condition undergoing treatment.

Monoclonal 5-62 and 25-1 were tested for competition against a variety of antisera.

| Monoclonal 5-62 and 25-1 were tested for competition against a variety of antisera LIST OF ANTIBODIES CHECKED FOR CROSSREACTIVITY AGAINST THE PAPP-A MONOCLONALS |
|---|
| DAKO ANTIBODIES |
| alphafetoprotein, albumin, a1-antichymotrypsin, antithrombin 111, a1-antitrypsin, C reactive protein, C1 esterase inhibitor, C3C complement, C3C(unspecific), C3d complement, C4 complement, cholinesterase, fibrinogen, fibronectin, human chorionic gonadotropin, human placental lactogen, inter-a-trypsin inhibitor, B-lipoproptein, a2-macroglobulin orosomucoid, PAPP-A, a2-plasmin inhibitor, plasminogen, pregnancy zone protein, schwangerschaftsprotein 1, placenta and B2-microglobulins. |

| -continued |
|---|
| Monoclonal 5-62 and 25-1 were tested for competition against a variety of antisera LIST OF ANTIBODIES CHECKED FOR CROSSREACTIVITY AGAINST THE PAPP-A MONOCLONALS |
| PROTEIN A-ISOLATED RABBIT SERUM |
| Pregnancy protein 12, pregnancy-associated plasma protein B, and chimp PAPP-A. |
| RABBIT SERUM |
| Human serum PAPP-A 1 & 2, chimp PAPP-A, rhesus PAPP-A, heparin-bound macaque LPS, macaque male serum, heparin-bound human male serum, heparin bound guinea pig placental homogenate, guinea pig placental proteins 1 & 2, seminal plasma, pregnancy protein 10, pregnancy protein 14, pregnancy protein 5, and inhibin. |
| MONOCLONAL ANTIBODY SUPERNATANTS |
| 25-1 IgG, 25-35 IgG,[1] 27-66 IgM, 27-105 IgM,[1] 5-62 IgG, 5-12 IgG,[1] 5-39 IgG,[1] 5-17 IgG,[1] 11-1-30 IgM,[2] |

The results indicate that the monoclonals recognize different epitopes.

TABLE 2

The results indicate that the monoclonals recongnize different epitopes.

| | % REDUCTION IN O.D. | |
|---|---|---|
| SPECIFICITY | 25-1 | 5-62 |
| Dako anti-PAPP-A | −78.4% | −91.9% |
| Dako anti-Placenta | −47.8% | −56.2% |
| Rabbit anti-Human serum PAPP-A 1 | −71.3% | −96.1% |
| Rabbit anti-Human serum PAPP-A 2 | −72.6% | −90.5% |
| Rabbit anti-Rhesus PAPP-A | −38.8% | −86.3% |
| Protein-A isolated anti-Chimp PAPP-A | −60.4% | −29.9% |
| 25-1 Monoclonal antibody supernatant | −50.8% | — |
| 25-35 Monoclonal antibody supernatant | −46.6% | — |
| 5-62 Monoclonal antibody supernatant | — | −61.7% |
| 5-23 Monoclonal antibody supernatant | — | −60.8% |
| 5-39 Monoclonal antibody supernatant | — | −62.6% |
| 5-17 Monoclonal antibody supernatant | — | −59.5% |

LIST OF REFERENCES

1. Lin, T. M., Halbert, S. P., and Kiefer, D.: Characterization and purification of human pregnancy associated plasma proteins. Fed. Proc. 32: 5232, 1973.
2. Sinosich, M. J., Teisner, B., Folkersen, J., et al.: Radioimmunoassay for pregnancy-associated plasma protein-A. Clin. Chem. 28: 50, 1982.
3. Wald, N., Stone, R., Cuckle, H. S., et al.: First trimester concentrations of pregnancy associated plasma protein A and placental protein 14 in Down's syndrome; BMJ Vol. 305, p-28 (1992).
4. Westergaard, J. G., Chemnitz, J., Teisner, B., et al.: Pregnancy-associated plasma protein-A: A possible marker in the classification of prenatal diagnosis of Cornelia de Longe Syndrome. Prenat.Diag 3:225, 1983.
5. Sinosich, M. J., Davey, M. W., Teisner, B. et al.:
    Comparative studies of pregnancy associated plasma protein-A and $_2$-macroglobulin using metal chelate chromatography. Biochem. Internatl. 7: 33, 1983.
6. Sinosich, M. J., Porter, R., Sloss, P., ed al.:
    Pregnancy associated plasma protein-A (PAPP-A) in human ovarian follicular fluid. J.Clin. Endocrinol. Metab. 58: 500, 1984.

7. Sinosich, M. J., King, M., Bonifacio, M., et al.: Pregnancy associated plasma protein-A in human seminal plasma. Prot.Biol.Fluids 32:289, 1985.
8. Tsakok, F. K. H. M., Koh,S., Chua, E. S., et al.: Prognostic significance of the new placental proteins in trophoblastic disease. Br. J. Obstet. Gynaecol. 90:483, 1983.
9. Davey, M., Teisner, B., Sinosich, M. J., et al: Interaction between heparin and human pregnancy associated plasma protein A: A simple purification procedure. Anal. Biochem. 131: 18, 1983.
10. Sinosich, M. J., Davey, M. W., Ghosh, P., et al. Specific inhibition of human granulocyte elastase by human pregnancy-associated plasma protein-A. Biochem. Internat. 5: 777, 1982.
11. Sinosich, M. J. and Saunders, D. M.,: Potential role for pregnancy-associated plasma protein-A in human reproduction. J. Reprod. Immunol. 10:55, 1987.
12. Sinosich, M. J., Saunders, D. M. and Grudzinskas, J. G.: Pregnancy-associated plasma protein A: a barrier to maternal proteolytic attack—*In In Vitro Fertilization, Embryo Transfer and Early Pregnancy* —Edited by R. F. Harrison, J. Bonnar and W. Thompson, Lancaster, MTP Press Ltd 1984, pp.209.
13. Schindler, A. M. and Bischof, P.: Histochemical localization of pregnancy-associated plasma protein-A in fetal, infant and adult organs and comparison between antisera. Gynecol. Obstet.Invest. 18:88, 1984.
14. Bischof, P., Herrmann, W. L. and Sizonenko, P. C.: Pulsatile secretion of pregnancy-associated plasma protein-A (PAPP-A) in non-pregnant women: Br. J. Obstet Gynecol 93:600, 1986.
15. Bischof, P., Reyes, H., Herrmann, W. L. et al.: Circulating levels of pregnancy-associated plasma protein-A (PAPP-A) and human chorionic gonadotrophin (hCG) in intrauterine and extrauterine pregnancies.: Br. J. Obstet. Gynecol 90:323, 1983.
16. Sinosich M. J. —Past, present and future of pregnancy associated plasma protein A—*In Placental and Endometrial Proteins.* Tomoda, Y., Mizutani, S., Norita, O. and Klopper, A. (eds). USP, 1988, pp.11.
17. Sinosich, M. J., Smith, D. H., Grudzinskas, J. G. et al. The prediction of pregnancy failure by measurement of pregnancy-associated plasma protein-A (PAPP-A) following IVF-ET. Fertil.Steril 40:539,1983.
18. Westergaard, J. G., Sinosich, M. J., Bugge, M., et al.: Pregnancy associated plasma protein A in the prediction of early pregnancy failure. Am. J. Obstet. Gynecol. 145: 67, 1983.
19. Sinosich, M. J., Ferrier, A., Saunders, D. M. —Monitoring of post-implantation embryo viability following successful in vitro fertilization and embryo transfer by measurement of placental proteins. Fertil. Steril. 44: 70. 1985.
20. Sinosich, M. J., Ferrier, A., Porter, R. N., et al. —Circulating and tissue concentrations of pregnancy-associated plasma protein-A (PAPP-A) in tubal eptopic gestation. J. Clin. Reprod.Fertil. 3:311, 1985.
21. Brambati, B., Lanzani, A., Tului, L., et al. —Ultrasound and biochemical assessment of first trimester of pregnancy—In—*The embryo: normal and abnormal development and growth*: Chapman, M., Grudzinskas, J. G., Chard, T. (eds) London, Springer-Verlag, pp. 181-94 (1990).
22. Lin et al. Characterisation of four human pregnancy associated plasma proteins. Am. J. Obstet. Gynecl. 18:223–26, 1974.
23. Lin, T. M., Holbert, S. P. and Kiefer, D.—Three pregnancy associated human plasma proteins: purification, monospecific anti-sera and immunological identification. Int. Archs. Allergy Appl. Immun. 47: 35 (1974).
24. Bischof, P.—Purification and characterization of pregnancy-associated plasma protein-A (PAPP-A): Arch. Gynecol. 227: 315–32 (1979)
25. Sutcliffe, R. G., Kukulska, B. M., Nicholson, L. V. B., et al. The use of antibody affinity chromatography and other methods in the study of pregnancy-associated proteins. In Placental Proteins (Klopper. A, and Chard T., eds. pp. 55–70, Springer-Verlag Berlin/New York.)
26. Folkersen, J., Grudzinskas, J. G., Hindersson, P. et al.—Purification of pregnancy-associated plasma protein-A by a two step affinity chromatographic procedure (1981). Placenta 2: 11, (1981).
27. Sinosich, M. J., Teisner, B., Davey, M., et al. Pregnancy-associated plasma protein-A: interaction with heparin in crossed affinity immunoelectrophoresis. Aust. N. Z. J. Med. 11: 429, (1981).
28. Sinosich, M. J.—Biological role of pregnancy-associated plasma protein-A in human reproduction. In Proteins of the Placenta—Bischof, P and Klopper, A (eds). Kasper, Basel. pp. 158 (1985).
29. Sinosich, M. J., Sim, R., Teisner, B. Characterization of pregnancy associated plasma protein-A: comparison with a 2-macroglobulin. Biochem Inter 20: 579, (1990).
30. Sinosich, M. J. & Zakher, A. Pregnancy-associated plasma protein-A (PAPP-A) interaction with heparin; A critical appraisal. Gynecol Obstet Invest 32:72, (1991).
31. Maniatis et al. (1984): Molecular Cloning. A Laboratory Manual. Cold Spring Harbor Laboratory Press.

What is claimed is:

1. A monoclonal antibody which binds to PAPP-A, wherein said PAPP-A used to generate the antibody is at least 90% pure.

2. The monoclonal antibody according to claim 1 which does not cross-react with immobilized heparin-Separose binding proteins extracted from normal male serum.

3. The monoclonal antibody according to claim 1 which is specific for PAPP-A.

4. The monoclonal antibody according to claim 1 which is an IgG or IgM antibody.

5. The monoclonal antibody according to claim 1 which has kappa light chains.

6. A monoclonal antibody produced by a clone selected from the group consisting of 25-1 and 18-9 or an immunoglobulin, or fragment thereof which recognizes the same epitope as a monoclonal antibody produced by said clone.

7. An immunoassay for PAPP-A comprising using a monoclonal antibody to detect PAPP-A, wherein said monoclonal antibody is raised against PAPP-A which is at least 90% pure and wherein said monoclonal antibody is selected from the group consisting of:
   (a) a monoclonal antibody which binds PAPP-A;
   (b) a monoclonal antibody which binds PAPP-A but does not cross-react with immobilized heparin-Sepharose binding proteins extracted from normal male serum;
   (c) a monoclonal antibody specific for PAPP-A;
   (d) a monoclonal antibody of (a), (b), or (c) which is an IgG or IgM antibody; and
   (e) a monoclonal antibody of (a), (b), or (c) which has kappa light chains.

8. An immunoassay according to claim 7 which is selected from the group consisting of an ELISA assay and an immunoradiometric assay.

9. An immunoassay according to claim 7 comprising a ligand selected from the group consisting of ligands which specifically bind with PAPP-A and ligands which bind with PAPP-A selected from the group consisting of heparin, divalent metal cations, lectins and dyes as capture phase.

10. An assay according to claim herein the monoclonal antibody may or may not be directly tagged.

11. An immunoassay according to claim 7 wherein said PAPP-A is bound to an immunoglobulin.

12. A method of detecting PAPP-A in a sample which comprises the steps of:
   (a) contacting the sample with a PAPP-A capture phase which consists of one or more of the following:
      (i) monoclonal PAPP-A antibody;
      (ii) polyclonal PAPP-A antibody;
      (iii) immobilized heparin;
      (iv) immobilized divalent metal cations;
      (v) immobilized lectins;
      (vi) dye ligands capable of binding PAPP-A; and
      (vii) receptors capable of binding PAPP-A;
   (b) contacting the immobilized or captured PAPP-A sample with a monoclonal antibody labelled with a detectable marker wherein said monoclonal antibody is raised against PAPP-A which is at least 90% pure and is selected from the group consisting of:
      (i) a monoclonal antibody which binds PAPP-A;
      (i) a monoclonal antibody which binds PAPP-A but does not cross-react with immobilized heparin-Sepharose binding proteins extracted from normal male serum;
      (iii) a monoclonal antibody specific for PAPP-A;
      (iv) a monoclonal antibody of (i), (ii) or (iii) which is an IgG or IgM antibody; and
      (v) a monoclonal antibody of (i), (ii), or (iii) which has kappa light chains;
   (c) incubating the sample and the labelled antibody to permit the labelled antibody to bind to any PAPP-A in the sample and;
   (d) detecting the labelled protein.

13. The method according to claim 12 wherein the immobilized divalent cation is selected from the group consisting of Cu++, Zn++, Co++ and Ni++.

14. The method according to claim 12 wherein the immobilised lectin is selected from the group consisting of Concanavalin A, *Helix pomatia, Lens culinaris, Limulis polyphemus*, phytohaemaglutinin, *Ricinus communis*, Wheat germ and other lectins which bind PAPP-A.

15. A kit for the detection of PAPP-A in a sample, said kit comprising at least one monoclonal antibody together with a positive control or a negative control, wherein said monoclonal antibody is raised against PAPP-A which is at least 90% pure, and wherein said monoclonal antibody is selected from the group consisting of:
   (a) a monoclonal antibody which binds PAPP-A;
   (b) a monoclonal antibody which binds PAPP-A but does not cross-react with immobilized heparin-Sepharose binding proteins extracted from normal male serum;
   (c) a monoclonal antibody specific for PAPP-A;
   (d) a monoclonal antibody of (a), (b), or (c) which is an IgG or IgM antibody; and
   (e) a monoclonal antibody of (a), (b), or (c) which has kappa light chains.

16. A method for prenatal fetal karyotyping comprising employing a PAPP-A monoclonal antibody for the isolation of trophoblast cells from maternal circulation or reproductive tract, wherein said monoclonal antibody is raised against PAPP-A which is at least 90% pure, and wherein said monoclonal antibody is selected from the group consisting of:
   (a) a monoclonal antibody which binds PAPP-A;
   (b) a monoclonal antibody which binds PAPP-A but does not cross-react with immobilized heparin-Sepharose binding proteins extracted from normal male serum;
   (c) a monoclonal antibody specific for PAPP-A;
   (d) a monoclonal antibody of (a), (b), or (c) which is an IgG or IgM antibody; and
   (e) a monoclonal antibody of (a), (b), or (c) which has kappa light chains.

17. A method of diagnosis of a clinical condition involving PAPP-A comprising employing a PAPP-A monoclonal antibody as a diagnostic reagent, wherein said monoclonal antibody is raised against PAPP-A which is at least 90% pure and wherein said monoclonal antibody is selected from the group consisting of:

(a) a monoclonal antibody which binds PAPP-A;

(b) a monoclonal antibody which binds PAPP-A but does not cross-react with immobilized heparin-Sepharose binding proteins extracted from normal male serum;

(c) a monoclonal antibody specific for PAPP-A;

(d) a monoclonal antibody of (a), (b), or (c) which is an IgG or IgM antibody; and (e) a monoclonal antibody of (a), (b), or (c) which has kappa light chains.

18. The method according to claim 17 wherein said condition is an oncological disorder.

19. The method according to claim 17 wherein said condition is a compromised pregnancy.

20. The method according to claim 17 where said condition is a malignant trophoblastic disease and said method involves prenatal screening.

21. The method according to claim 17 where said condition is Down's Syndrome and said method involves prenatal screening.

22. An immunoassay for PAPP-A comprising using a monoclonal antibody to detect PAPP-A, said monoclonal antibody selected from the group consisting of 25-1 and 18-9 or an immunoglobulin or fragment thereof which recognizes the same epitope as a monoclonal antibody produced by said clone.

23. An immunoassay according to claim 22 which is selected from the group consisting of an ELISA assay and an immunoradiometric assay.

24. An immunoassay according to claim 22 comprising a ligand selected from the group consisting of ligands which specifically bind with PAPP-A and ligands which bind with PAPP-A selected from the group consisting of heparin, divalent metal cations, lectins and dyes as capture phase.

25. An immunoassay according to claim 22 wherein the monoclonal antibody is optionally tagged.

26. An immunoassay according to claim 22 wherein said PAPP-A is bound to an immunoglobulin.

27. A kit for the detection of PAPP-A in a sample, said kit comprising at least one monoclonal antibody and at least one control selected from the group consisting of a positive control and a negative control, wherein said monoclonal antibody is produced by a clone selected from the group consisting of 25-1 and 18-9 or an immunoglobulin, or fragment thereof which recognizes the same epitope as a monoclonal antibody produced by said clone.

28. A method for prenatal fetal karyotyping comprising employing a PAPP-A monoclonal antibody for the isolation of trophoblast cells from maternal circulation or reproductive tract, wherein said monoclonal antibody is produced by a clone selected from the group consisting of 25-1 and 18-9 or an immunoglobulin, or fragment thereof which recognizes the same epitope as a monoclonal antibody produced by said clone.

29. A method of diagnosis of a clinical condition involving PAPP-A comprising using a PAPP-A monoclonal antibody as a diagnostic reagent, wherein said monoclonal antibody is produced by a clone selected from the group consisting of 25-1 and 18-9 or an immunoglobulin or fragment thereof which recognizes the same epitope as a monoclonal antibody produced by said clone.

30. An immunoassay for detecting the presence of an anti-PAPP-A antibody in a sample comprising the steps of;

(a) contacting the sample with PAPP-A so that any anti-PAPP-A antibody present in the sample is bound to PAPP-A;

(b) binding a monoclonal antibody to said PAPP-A, wherein said monoclonal antibody is produced by a clone selected from the group consisting of 25-1 and 18-9 or an immunoglobulin, or fragment thereof which recognizes the same epitope as a monoclonal antibody produced by said clone; and (c) detecting said monoclonal antibody, wherein the detection of said monoclonal antibody indicates the presence of anti-PAPP-A antibody in the sample.

31. An immunoassay according to claim 30 wherein said monoclonal antibody is labelled and said monoclonal antibody is detected by detecting the label.

32. An immunoassay according to claim 30 wherein said monoclonal antibody is fixed to a solid support.

33. An immunoassay for detecting the presence of an anti-PAPP-A antibody in a sample comprising the steps of:

(a) providing PAPP-A bound to a monoclonal antibody wherein said monoclonal antibody is produced by a clone selected from the group consisting of 25-1 and 18-9 or an immunoglobulin, or fragment thereof which recognizes the same epitope as a monoclonal antibody produced by said clone;

(b) contacting the sample with said PAPP-A so that any anti-PAPP-A antibody in the sample binds to said PAPP-A, (c) detecting said monoclonal antibody; wherein the detection of said monoclonal antibody indicates the presence of anti-PAPP-A antibody in the sample.

34. An immunoassay according claim 33 wherein the monoclonal antibody bound to PAPP-A is labelled and said monoclonal antibody is detecting by detecting the label.

35. An immunoassay according to claim 33 wherein said monoclonal antibody is fixed to a solid support.

* * * * *

UNITED STATES PATENT AND TRADEMARK OFFICE
CERTIFICATE OF CORRECTION

PATENT NO. : 6,172,198
DATED : January 9, 2001
INVENTOR(S) : Michael J. Sinosich It is certified that error appears in the above-identified patent and that said Letters Patent is hereby corrected as shown below:

Col. 4, line 29, replace "[SEQ ID NO:9]" with -- [SEQ ID NO:1] -- .

Col. 6, line 14, replace "(Cu++, Zn++, Co++, Ni++);" with -- ($Cu^{++}$, $Zn^{++}$, $Co^{++}$, $Ni^{++}$); -- .

Signed and Sealed this

Fifteenth Day of May, 2001

NICHOLAS P. GODICI

*Attest:*

*Attesting Officer*   *Acting Director of the United States Patent and Trademark Office*